US008871712B2

(12) United States Patent
Joabsson et al.

(10) Patent No.: US 8,871,712 B2
(45) Date of Patent: Oct. 28, 2014

(54) SOMATOSTATIN ANALOGUE FORMULATIONS

(75) Inventors: Fredrik Joabsson, Lund (SE); Markus Johnsson, Lund (SE); Andreas Norlin, Lund (SE); Fredrik Tiberg, Lund (SE)

(73) Assignee: Camurus AB (SE)

( * ) Notice: Subject to any disclaimer, the term of this patent is extended or adjusted under 35 U.S.C. 154(b) by 710 days.

(21) Appl. No.: 11/795,249

(22) PCT Filed: Dec. 9, 2005

(86) PCT No.: PCT/GB2005/004748
§ 371 (c)(1),
(2), (4) Date: Feb. 28, 2008

(87) PCT Pub. No.: WO2006/075124
PCT Pub. Date: Jul. 20, 2006

(65) Prior Publication Data
US 2009/0069221 A1  Mar. 12, 2009

(30) Foreign Application Priority Data

Jan. 14, 2005 (GB) .................................. 0500807.3
Apr. 18, 2005 (GB) .................................. 0507811.8
Jun. 6, 2005 (WO) ............... PCT/GB2005/002217
Sep. 15, 2005 (GB) .................................. 0518878.4

(51) Int. Cl.
*A61K 38/31* (2006.01)
*A61P 5/02* (2006.01)
*C07K 14/655* (2006.01)
*A61K 38/12* (2006.01)
*C07K 14/65* (2006.01)

(52) U.S. Cl.
CPC ................. *A61K 38/12* (2013.01); *C07K 14/65* (2013.01); *A61K 38/31* (2013.01)
USPC ....................................................... 514/11.1

(58) Field of Classification Search
CPC ................................ C07K 14/65; A61K 38/31
See application file for complete search history.

(56) References Cited

U.S. PATENT DOCUMENTS

| 4,938,763 | A | | 7/1990 | Dunn et al. |
| 5,340,802 | A | | 8/1994 | Shiosaki et al. |
| 5,480,656 | A | | 1/1996 | Okada et al. |
| 5,531,925 | A | | 7/1996 | Landh et al. |
| 5,639,480 | A | * | 6/1997 | Bodmer et al. ............... 424/501 |
| 5,776,885 | A | | 7/1998 | Orsolini et al. |
| 5,807,573 | A | | 9/1998 | Ljusber-Wahren et al. |
| 5,955,502 | A | | 9/1999 | Hansen et al. |
| 6,066,328 | A | | 5/2000 | Ribier et al. |
| 6,113,943 | A | | 9/2000 | Okada et al. |
| 6,228,383 | B1 | | 5/2001 | Hansen et al. |
| 6,458,924 | B2 | | 10/2002 | Knudsen et al. |
| 6,464,987 | B1 | | 10/2002 | Fanara et al. |
| 8,097,239 | B2 | | 1/2012 | Johnsson et al. |
| 8,182,834 | B2 | | 5/2012 | Johnsson et al. |
| 8,187,629 | B2 | | 5/2012 | Barauskas et al. |
| 8,236,292 | B2 | | 8/2012 | Thuresson et al. |
| 8,236,755 | B2 | | 8/2012 | Thuresson et al. |
| 2002/0026027 | A1 | | 2/2002 | Ansell |
| 2003/0022242 | A1 | | 1/2003 | Anderson |
| 2004/0018241 | A1 | | 1/2004 | Houze et al. |
| 2004/0201117 | A1 | | 10/2004 | Anderson |
| 2005/0136059 | A1 | | 6/2005 | Thorpe et al. |
| 2006/0073203 | A1 | | 4/2006 | Ljusberg-Wahren et al. |
| 2007/0080323 | A1 | | 4/2007 | Joabsson et al. |
| 2007/0110777 | A1 | | 5/2007 | Joabsson et al. |
| 2007/0134336 | A1 | | 6/2007 | Worle et al. |
| 2007/0231374 | A1 | | 10/2007 | Tiberg et al. |
| 2008/0124394 | A1 | | 5/2008 | Johnsson et al. |
| 2008/0146490 | A1 | | 6/2008 | Joabsson et al. |
| 2008/0161276 | A1 | | 7/2008 | Johnsson et al. |
| 2008/0214995 | A1 | | 9/2008 | Boyd et al. |
| 2008/0274176 | A1 | | 11/2008 | Johnsson et al. |
| 2009/0155193 | A1 | | 6/2009 | Joabsson et al. |
| 2009/0170782 | A1 | | 7/2009 | Joabsson et al. |
| 2010/0210519 | A1 | | 8/2010 | Johnsson et al. |
| 2011/0230569 | A1 | | 9/2011 | Nistor et al. |
| 2012/0028890 | A1 | | 2/2012 | Nistor et al. |
| 2012/0269772 | A1 | | 10/2012 | Thuresson et al. |

FOREIGN PATENT DOCUMENTS

| EP | 1600162 | 11/2005 |
| WO | 93/06921 | 4/1993 |
| WO | WO 95/34287 A1 | 12/1995 |
| WO | 97/13528 | 4/1997 |

(Continued)

OTHER PUBLICATIONS

Definition of analog from http://cancerweb.ncl.ac.uk/omd/about.html, pp. 1-5. Accessed Jul. 7, 2005.*
E. Woltering et al., "Octreotide acetate (LAR) dose effect on plasma octreotide levels: Impact on neuroendocrine tumor management", F. Clin Oncology, 2005 ASCO Annual Meeting Proceedings, vol. 23, No. 16S, pp. 3177, (Abstract only).
A. K. ;Flogstad et al., "Sandostatin LAR in acromegalic patients: long term treatment.", J. Clinical Endorinology & Metabolism, 1997, vol. 82, No. 1, pp. 23-28.

(Continued)

*Primary Examiner* — Marcela M Cordero Garcia
*Assistant Examiner* — Kaipeen Yang
(74) *Attorney, Agent, or Firm* — J.A. Lindeman & Co., PLLC

(57) ABSTRACT

Pre-formulations of a low viscosity mixture containing: a) at least one diacyl glycerol; b) at least one phosphatidyl choline; c) at least one oxygen containing organic solvent; d) at least one somatostatin analog are described. The pre-formulation forms, or is capable of forming, at least one liquid crystalline phase structure upon contact with an aqueous fluid. The pre-formulations are useful for generating depot composition far the controlled release of somatostatin analogs such as octreotide. Methods of treatment comprising the administration of such formulations are also provided, as are pre-filled administration devices and kits containing the formulations.

33 Claims, 4 Drawing Sheets

(56) References Cited

FOREIGN PATENT DOCUMENTS

| WO | 98/47487 | 10/1998 |
|---|---|---|
| WO | WO 02/02716 A2 | 1/2002 |
| WO | WO 02/066014 A2 | 8/2002 |
| WO | WO 02/068561 A2 | 9/2002 |
| WO | WO 02/068562 A2 | 9/2002 |
| WO | WO 03/002136 A2 | 1/2003 |
| WO | WO 03/057235 A2 | 7/2003 |
| WO | WO 2004/087215 A1 | 10/2004 |
| WO | WO 2005/014162 A1 | 2/2005 |
| WO | WO 2005/021022 A2 | 3/2005 |
| WO | 2005/046642 | 5/2005 |
| WO | WO 2005/048952 A2 | 6/2005 |
| WO | WO 2005/063213 A1 | 7/2005 |
| WO | 2005/070394 | 8/2005 |
| WO | WO 2005/117830 A1 | 12/2005 |
| WO | WO 2006/075123 A1 | 7/2006 |
| WO | WO 2006/075124 A1 | 7/2006 |
| WO | WO 2006/075125 A1 | 7/2006 |
| WO | WO 2006/077362 A1 | 7/2006 |
| WO | WO 2006/131730 A1 | 12/2006 |
| WO | WO 2008/152401 A1 | 12/2008 |
| WO | WO 2009/024795 A1 | 2/2009 |
| WO | WO 2009/024797 A1 | 2/2009 |
| WO | WO 2010/020794 A1 | 2/2010 |

OTHER PUBLICATIONS

P. Chanson et al., "Comparison of octreotide acetate LAR and lanreptide SR in patients with acromegaly.", Clin. Endocrinology, 2001, vol. 54, No. 1, pp. 11-13, (Abstract only).

N. Ardjomand et al., "Expression of Somatostatin Receptors in uveal melanomas.", Inv. Opthalmol. & Vis. Sci., 2003, vol. 44, No. 3, pp. 980-987.

B. L. Erstad, "Octreotide for acute variceal bleeding.", Ann. Pharmacother., 2001, vol. 35, No. 5, pp. 618-626. (Abstract only).

I. Lancranjan et al., "Sandostatin LAR: Pharmacokinetics, Pharmacodynamis, Efficacy and Tolerability in Acromegalic Patients.", Metabolism, 1995, vol. 44, No. 1, pp. 18-26.

Welin et al., "High-dose treatment with a long-acting somatostatin analogue in patients with advanced midgut carcinoid tumours", 2004, Society of the European Journal of Endocrinology, vol. 151, pp. 107-112.

Comets et al., "Nonparametric analysis of the absorption profile of octreotide in rabbits from long-acting release formulation OncoLAR", Journal of controlled release, 1999, vol. 59, pp. 197-205.

Barauskas et al., Pharmaceutical Nanotechnology, "Interactions of lipid-based liquid crystalline nanoparticles with model and cell membranes," International Journal of Pharmaceutics 391 (2010) pp. 284-291.

R. Berges, "Eligard: Pharmacokinetics, Effect on Testosterone and PSA Levels and Tolerability," European Urology Supplements, 2005, vol. 4, pp. 20-25.

Chang, J., "Use of GnRH agonists in the treatment of hyperandrogenism and hirsutism," print out from http://patients.uptodate.com.

Comets et al., "Non parametric analysis of the absorption profile of octreotide in rabbits from long-acting release formulation OncoLAR," J. Controlled Release 59:197-205 (1999).

FDA's 510(k) Summary of Camurus AB, episil® K101769.

P. R. Gibson & J. G. Muir, "Reinforcing the mucus: a new therapeutic approach for ulcerative colitis," Gut, 2005, vol. 54, pp. 900-903.

L. M. Grant & F. Tibert, "Normal and Lateral Forces between Lipid Covered Solids in Solution: Correlation with Layer Packing and Structure," Biophysical Journal, 2002, vol. 82, pp. 1373-1385.

B.A. Hills, "Surface-active phospholipid: a Pandora's box of clinical applications. Part II. Barrier and lubricating properties," Internal Medicine Journal, 2002, vol. 32, pp. 242-251.

G. G. Holz et al., "Glucagon-Like Peptide-1 Synthetic Analogs: New Therapeutic Agents for Use in the Treatment of Diabetes Mellitus," Current Medicinal Chemistry (2003), vol. 10, pp. 2471-2483.

H. Hui et al., "Structure and function studies of glucagon-like peptide-1 (GLP-1): the designing of a novel pharmacological agent for the treatment of diabetes," Diabetes Metabolism Research and Reviews, (2005), vol. 21, pp. 313-331.

Indications and Usage of Eligard, pp. 1-5, print out from http:ffwww.rxlist.com.

Information About Buprenorphine Therapy, print out from http://buprenorphine.samhsa.gov/about.html, pp. 1-4.

Information on Goserelin Acetate print out form http://www.bachem.com/.

Information on Goserelin Subcutaneous, Monograph—Goserelin Acetate, pp. 1-7, print out form www.medscape.com.

Information on Leuprolide Intramuscular, Monograph—Leuprolide Acetate, pp. 1-20, print out for www.medscape.com.

Information on Leuprolide (3 Month) Intramuscular, Monograph—Leuprolide Acetate, pp. 1-20, print out from www.medscape.com.

Invitrogen, "Pluronic F-127," Molecular Probes Invitrogen Detection Technologies, pp. 1-2, 2008.

Johnsson et al., "Physicochemical and Drug Delivery Aspects of Lipid-Based Liquid Crystalline Nanoparticles: A Case Study of Intravenously Administered Propofol," Journal of Nanoscience and Nanotechnology, vol. 6, No. 9/10, pp. 3017-3024, 2006.

Kamo, et al., "Nonlamellar Liquid Crystalline Phases and Their Particle Formation in the Egg Yolk Phosphatidylcholine/Diolein System," Langmuir, vol. 19, pp. 9191-9195, Published on Web Oct. 1, 2003.

Kesisoglou, et al., "Liposomal Formulations of Inflammatory Bowel Disease Drugs: Local versus Systemic Drug Delivery in a Rat Model," Pharmaceutical Research, vol. 22, No. 8, Aug. 2005, pp. 1320-1329.

J. G. M. Klijn et al., "Combined tamoxifen and luteinizing hormone-releasing hormone (LHRH) agonist versus LHRH agonist alone in premenopausal advanced breast cancer: A meta-analysis of four randomized trials," Journal of Clinical Oncology, 2001, vol. 19, No. 2, pp. 343-353 (Abstract only).

L. M. Knudsen, "Glucagon-like Peptide-1: The Basis of a New Class of Treatment for Type 2 Diabetes," J. Med. Chem. (2004), vol. 47, pp. 4128-4134.

L. M. Knudsen et al., "Potent Derivatives of Glucagon-like Peptide-1 with Pharmacokinetic Properties Suitable for Once Daily Administration," J. Med. Chem. (2000) vol. 43, pp. 1664-1669.

"Leutinizing Hormone Releasing Hormone (LHRH) Agonists: Goserelin (Zoladex) vs. Leuprolide (Lupron) for Prostate Cancer," DoD Pharmacoeconomic Center Update, Newsletter, Dec. 2000, vol. 1, No. 1, print out from http://www.pec.ha.osd.mil.com, pp. 1-3.

Loughrey et al., "Development of a Sensitive Sandwich ELISA for Detecting Full Length Biologically Active TH0318, a GLP-1 Analogue," presented at the 2005 AAPS Annual Meeting and Exposition, Abstract No. W5009.

Martel et al., "Enzyme Linked Immunosorbent Assay (EUSA) Method for the Determination of TH0318, a New GLP-1 Analogue in Development for Diabetes," presented at the 2005 MPS Annual Meeting and Exposition, Abstract No. W5008.

Martel et al., "Enzyme Linked Immunosorbent Assay (EUSA) Method for the Determination of TH0318, a New GLP-1 Analogue in Development for Diabetes," Poster.

MSDS for Ethylene Glycol and Abbreviations used in Toxicity data.

PDR Information on Eligard 30 mg (Sanofi-Synthelabo), print out from www.Drugs.com, pp. 1-14.

Pharmaceutical Information on Lupron Depot, print out from www.rxmed.com, pp. 1-8.

Product Information on Zoladex Goserelin Acetate Implant (Equivalent to 10.8 mg goserelin).

Product Specification of Leuprolide by GL Biochem, print out from http://www.glschina.com.

O. Sartor "Eligard: Leuprolide Acetate in a Novel Sustained-Release Delivery System," Urology, 2003, vol. 61, (Supplement 2A), pp. 25-31.

K. J. Schuh et al., "Onset, magnitude and duration of opioid blockade produced by buprenorphine and naltrexone in humans," Psychopharmacology, (Berl ), Jul. 1999, vol. 145, No. 2, pp. 162-174 (Abstract only).

(56) References Cited

OTHER PUBLICATIONS

J. C. Shah et al., "Cubic phase gels as drug delivery systems," Advanced Drug Delivery Reviews, 2001, vol. 47, pp. 229-250.
W. Stremmel et al., "Retarded release phosphatidylcholine benefits patients with chronic active ulcerative colitis," Gut, 2005, vol. 54, pp. 966-971.
A Sturm & A. U. Dignass, "Modulation of gastrointestinal wound repair and inflammation by phospholipids," Biochimica et Biophysica Acta, 2002, vol. 1582, pp. 282-288.
Svanberg et al., "A New Preventive Strategy Using a Bioadhesive Oromucosal Lipid Solution and Oral Cryotherapy to Protect the Oral Cavity—and Reduce the Need for Total Parenteral Nutrition (Tpn) for Patients Undergoing Autologous Stemcell Transplantation," Support Care Cancer 18 (Suppl 3):S114-S115, at Abstract 08-076 (2010) (attached hereto as Annex 5 to Evidentiary Declaration Under 37 C.F.R. § 1.132 of Fredrik Tiberg).
Tiberg et al., "Drug delivery applications of non-lamellar liquid crystalline phases and nanoparticles", J. Drug Del Sci. Tech., 21(1) pp. 101-109, 2011.
Tiberg et al., "Treatment of oral mucositis pain by a bioadhesive barrier forming lipid solution," Camurus (attached hereto as Annex 3 to Evidentiary Declaration Under 37 C.F.R. § 1.132 of Fredrik Tiberg).
Tiberg et al., "Treatment of Oral Mucositis Pain by a Bioadhesive Barrier Forming Lipid Solution," Support Care Center 17(7):918 (2009) (attached hereto as Annex 4 to Evidentiary Declaration Under 37 C.F.R. § 1.132 of Fredrik Tiberg).
Wermuth, Pure and Appl. Chem, 1998, 70, 1129-1143.
International Search Report of PCT/GB2005/004745 dated May 8, 2006.
International Preliminary Report on Patentability of PCT/GB2005/004745 dated Jul. 20, 2007.
Written Opinion of PCT/GB2005/004745 dated May 8, 2006.
International Search Report of PCT/GB2005/04748 dated Mar. 23, 2006.
International Preliminary Report on Patentability of PCT/GB2005/04748 dated Mar. 12, 2007.
Written Opinion of PCT/GB2005/04748 dated Mar. 23, 2006.
International Search Report of PCT/GB2005/04752 dated Mar. 17, 2006.
International Preliminary Report on Patentability of PCT/GB2005/04752 dated Mar. 12, 2007.
Written Opinion of PCT/GB2005/04752 dated Mar. 17, 2006.
International Search Report of PCT/GB2005/004746 dated Mar. 16, 2006.
International Preliminary Report on Patentability and Written Opinion of PCT/GB2005/004746 dated Jul. 17, 2007.
International Search Report of PCT/GB2006/002079 dated Aug. 25, 2006.
International Preliminary Report on Patentability and Written Opinion of PCT/GB2006/002079 dated Dec. 6, 2007.
International Search Report of PCT/GB2008/002035 dated Oct. 6, 2008.
International Preliminary Report on Patentability of PCT/GB2008/002035 Dec. 17, 2009.
Written Opinion of PCT/GB2008/002035 dated Oct. 6, 2008.
International Search Report of PCT/GB2008/002857 dated Jan. 28, 2009.
International Preliminary Report on Patentability and Written Opinion of PCT/GB2008/002857 dated Feb. 24, 2010.
International Search Report of PCT/GB2009/002054 dated Nov. 30, 2009.
International Preliminary Report on Patentability and Written Opinion of PCT/GB2009/002054 dated Feb. 22, 2011.
Office Action in U.S. Appl. No. 11/795,243 dated May 12, 2011.
Office Action in U.S. Appl. No. 11/795,243 dated Mar. 22, 2012.
Office Action in U.S. Appl. No. 11/795,250 dated Dec. 21, 2012.
Office Action in U.S. Appl. No. 11/795,250 dated Mar. 18, 2011.
Office Action in U.S. Appl. No. 11/795,250 dated Jun. 24, 2010.
Office Action in U.S. Appl. No. 11/795,242 dated Jan. 10, 2013.
Office Action in U.S. Appl. No. 11/795,242 dated Dec. 23, 2011.
Office Action in U.S. Appl. No. 11/908,740 dated Feb. 14, 2012.
Office Action in U.S. Appl. No. 11/877,935 dated Dec. 21, 2010.
Apr. 23, 2014, Office Action in U.S. Appl. No. 11/795,243.

\* cited by examiner

SEQUENCE LISTING

```
<160> NUMBER OF SEQ ID NOS: 2

<210> SEQ ID NO 1
<211> LENGTH: 14
<212> TYPE: PRT
<213> ORGANISM: Homo sapiens

<400> SEQUENCE: 1

Ala Gly Cys Lys Asn Phe Phe Trp Lys Thr Phe Thr Ser Cys
1               5                   10

<210> SEQ ID NO 2
<211> LENGTH: 4
<212> TYPE: PRT
<213> ORGANISM: Homo sapiens

<400> SEQUENCE: 2

Phe Trp Lys Thr
1
```

SOMATOSTATIN ANALOGUE FORMULATIONS

SEQUENCE LISTING

The instant application contains a Sequence Listing which has been submitted in ASCII format via EFS-Web and is hereby incorporated by reference in its entirety. Said ASCII copy, created on Apr. 25, 2011, is named 110002US.txt and is 792 bytes in size.

The present invention relates to formulation precursors (pre-formulations) for the in situ generation compositions for the controlled release of somatostatin analogues. In particular, the invention relates to pre-formulations of amphiphilic components and at least one somatostatin analogue for parenteral application, which undergo phase transition upon exposure to aqueous fluids, such as body fluids, thereby forming a controlled release matrix.

Many bioactive agents including pharmaceuticals, nutrients, vitamins and so forth have a "functional window". That is to say that there is a range of concentrations over which these agents can be observed to provide some biological effect. Where the concentration in the appropriate part of the body (e.g. locally or as demonstrated by serum concentration) falls below a certain level, no beneficial effect can be attributed to the agent. Similarly, there is generally an upper concentration level above which no further benefit is derived by increasing the concentration. In some cases increasing the concentration above a particular level results in undesirable or even dangerous effects.

Some bioactive agents have a long biological half-life and/or a wide functional window and thus may be administered occasionally, maintaining a functional biological concentration over a substantial period of time (e.g. 6 hours to several days). In other cases the rate of clearance is high and/or the functional window is narrow and thus to maintain a biological concentration within this window regular (or even continuous) doses of a small amount are required. This can be particularly difficult where non-oral routes of administration (e.g. parenteral administration) are desirable since self-administration may be difficult and thus cause inconvenience and/or poor compliance. In such cases it would be advantageous for a single administration must provide active agent at a therapeutic level over the whole period during which activity is needed.

Somatostatin is a 14 residue cyclic peptide hormone having the sequence Ala-Gly-Cys-Lys-Asn-Phe-Phe-Trp-Lys-Thr-Ser-Cys(SEQ ID NO: 1), where the two cystine residues are connected by a disulphide bridge to generate a type II β-turn at the key binding sequence of Phe-Trp-Lys-Thr (SEQ ID NO: 2). Somatostatin is a natural peptide hormone also known as Growth Hormone Release Inhibiting Factor and has a role as an antagonist of insulin, glucogen and certain other hormones in the release of somatotrophin (Human Growth Hormone). The biological half-life of natural Somatostatin is very short (1-3 minutes) and so it is not, in itself, a viable therapeutic but an increasing number of somatostatin analogues are becoming available with higher activities and/or longer clearance times in vivo.

Somatostatin analogues, such as octreotide, lanreotide, vapreotide and related peptides, are used or indicated in the treatment of a variety of conditions where they are typically administered over an extended period.

Octreotide, for example, is the synthetic octa-peptide with sequence D-Phe-Cys-Phe-D-Trp-Lys-Thr-Cys-Thr-ol (2-7 disulphide bridge) and is typically administered as the acetate salt. Several clinical studies also feature the octreotide pamoate. This derivative retains the key Phe-(D)Trp-Lys-Thr β-turn but, in contrast to the natural hormone, has a terminal half-life of around 1.7 hours. Octreotide is used in treatment of conditions including carcinoid tumours and acromegaly, and after an initial dose is typically given over a sustained period of weeks, or more commonly many months or years. In addition, somatostatin analogues are indicated in the treatment of many cancers since a wide variety of tumours are found to express somatostatin receptors. Of particular interest are those expressing the "sst(2)" and/or "sst(5)" receptor.

The most common "simple" formulation of Octreotide is the "SANDOSTATIN"® formulation from Novartis. This is a solution for subcutaneous (s.c) injection and a 100 µg dose reaches a peak concentration of 5.2 ng/ml at 0.4 hours post injection. The duration of action can be up to 12 hours but S.C. dosing is generally carried out every 8 hours. Evidently, S.C. injection 3 times daily for periods of months or years is not an ideal dosing regime.

In order to avoid the need for multiple daily injections of octreotide, a further formulation is available; "SANDOSTATIN LAR"® formulation, again from Novartis. This is a formulation of octreotide in poly lactic co-glycolic acid microspheres which, after resuspension, may be administered by intra muscular (i.m.) injection.

Carcinoid tumours are intestinal tumour arising from specialised cells with paracrine functions (APUD cells). The primary tumour is commonly in the appendix, where it is clinically benign. Secondary, metastatic, intestinal carcinoid tumours secrete excessive amounts of vasoactive substances, including serotonin, bradykinin, histamine, prostaglandins, and polypeptide hormones. The clinical result is carcinoid syndrome (a syndrome of episodic cutaneous flushing, cyanosis, abdominal cramps, and diarrhea in a patient with valvular heart disease and, less commonly, asthma and arthropathy). These tumours may grow anywhere in the gastrointestinal tract (and in the lungs) with approximately 90% in the appendix. The remainder occurs in the ileum, stomach, colon or rectum. Currently, treatment of carcinoid syndrome starts with i.v. bolus injection followed by i.v. infusion. When sufficient effect on symptoms has been established, treatment with a depot formulation of octreotide formulated in ploy lactic-co-glycolic acid (PLGA) microspheres is started. However, during the first two weeks or more after injection of the depot, daily s.c. injections with octreotide are recommended to compensate for the slow release from the PLGA spheres.

Acromegaly is a rare chronic and insidious hormonal disorder that occurs when the pituitary gland produces excess growth hormone (GH). It most commonly affects middle-aged adults and may lead to premature death.

Diabetes mellitus, hypertension, and increased risk of cardiovascular disease are the most serious health consequences of acromegaly. In addition, patients with acromegaly are at an increased risk of developing colon polyps, which can become cancerous. The prevalence of acromegaly is approximately 60 cases per million population, and the incidence is 3.3 new cases per million per year. The word acromegaly comes from the Greek words for "extremities" (acro) and "great" (megaly), because one of the most common symptoms of this condition is abnormal growth of the hands and feet.

Acromegaly is caused by prolonged overproduction of growth hormone (GH) and excessive production of insulin-like growth factor-I (IGF-I). In 98 percent of cases, the overproduction of GH is caused by a pituitary adenoma. The rate of GH production and the aggressiveness of the tumour vary from patient to patient. Generally, more aggressive tumours are seen in younger patients.

Acromegaly is a severe disease often diagnosed late. Morbidity and mortality rates are high, in particular, because of associated cardiovascular, cerebrovascular, and respiratory disorders and malignancies.

Treatment of acromegaly is initiated by a period of s.c. injections three times per day (optimal daily dose=300 µg octreotide). After the last s.c. dose and providing a suitable effect is observed then treatment with a depot formulation of octreotide formulated in poly lactic-co-glycolic acid (PLGA) microspheres is started. Dose adjustments are made after measurement of biomarkers (HG and IGF-1), typically after around 3 months.

The existing octreotide slow release formulation relies upon a well-established degrading-polymer type of depot formulation. Typically such formulations are based on a biodegradable polymer such poly (lactic acid) (PLA) and/or poly (lactic-co-glycolic acid) (PLGA) and may be in the form of a solution in an organic solvent, a pre-polymer mixed with an initiator, encapsulated polymer particles or (as in the case of octreotide) polymer microspheres.

The polymer or polymer particles entrap the active agent and are gradually degraded releasing the agent by slow diffusion and/or as the matrix is absorbed. Examples of such systems include those described in U.S. Pat. No. 4,938,763, U.S. Pat. No. 5,480,656 and U.S. Pat. No. 6,113,943 and can result in delivery of active agents over a period of up to several months. These systems do, however, have a number of limitations including the complexity of manufacturing and difficulty in sterilising (especially the microspheres). The local irritation caused by the lactic and/or glycolic acid which is released at the injection site is also a noticeable drawback. There is also often quite a complex procedure to prepare the injection dose from the powder precursor.

One highly significant drawback of the known PLGA octreotide depot system is the complexity of preparation for the administering person. The depot is provided as a powder precursor of the octreotide-containing microspheres, plus a diluent in which these must be uniformly suspended. Successful preparation of the depot system for administration requires a multi-step method which must be followed precisely in order to ensure that the powder-precursor is completely saturated and in a uniform suspension prior to injection. The depot system must then be administered immediately by a method involving continual rocking of the syringe to maintain a uniform dispersion up to the point of deep gluteal intramuscular injection.

A further limitation of the existing PLGA octreotide depot systems is that dosing cannot easily be taylored to suit particular patients. It has recently been proposed that dosing of somatostatin analogues should be relative to the body weight of the subject since plasma concentrations have shown a marked variability by subject weight. A depot system comprising a pre-weighted dry powder which is suspended unstabily in an injection vehicle does not allow any such control, however, unless a considerable range of pre-measured doses is to be provided. The suspension cannot be partially administered because the particles are not evenly suspended. It would thus be a considerable advantage to have a homogeneous depot precursor which allowed administration of a dose to be decided on a subject-specific basis at the time of administration.

From a drug delivery point of view, polymer depot compositions generally have the disadvantage of accepting only relatively low drug loads and having a "burst/lag" release profile. The nature of the polymeric matrix, especially when applied as a solution or pre-polymer, causes an initial burst of drug release when the composition is first administered. This is followed by a period of low release, while the degradation of the matrix begins, followed finally by an increase in the release rate to the desired sustained profile. This burst/lag release profile can cause the in vivo concentration of active agent to burst above the functional window immediately following administration, then drop back through the bottom of the functional window during the lag period before reaching a sustained functional concentration. Evidently, from a functional and toxicological point of view this burst/lag release profile is undesirable and could be dangerous. It may also limit the equilibrium concentration which can be provided due to the danger of adverse effects at the "peak" point.

In the case of octreotide, the functional window ranges from around 0.8 to 20+ ng/ml. A recent clinical study indicates that higher values are effective in patients with mid-gut carcinoid tumours and high-dose treatment may be an important addition to the current therapeutic arsenal for patients with advanced progressive midgut carcinoid tumours Welin et al. (European Journal of Endocrinology 151 (2004) 107-112.) Even so, as indicated above, the use of PLGA microspheres causes a lag of several weeks during which "top-up" injections must be provided. Evidently, it would be an advantage to provide a depot system which achieved a "plateau" level more quickly. The release of octreotide into rabbits from a PLGA microsphere product was studied by Comets et al (J. Controlled Release 59 (1999) 197-05), for example, and this indicated the "third phase" release of over 85% of the active agent began more than 15 days after administration.

The low loading capacity of polymeric depot products, as well as the nature of microparticles causes additional problems in administration. In particular, a relatively high volume, of around 5 ml must be injected in order to carry the microparticle suspension, and the suspension can easily block syringe needles (hence the need for adherence to strict administration protocols), thus requiring that a relatively wide (e.g. 19-gauge) needle be used. Both of these factors, as well as the need for deep i.m. injection, result in considerable discomfort to the patient during administration. It would be a considerable advantage if a depot system could be provided requiring lower volumes of administration, which was administrable through a narrower gauge needle, and/or did not require such deep injection.

The manufacture of PLGA microbeads is additionally a considerable difficulty with existing somatostatin analogue depot systems. In particular, since the beads are particulate, they cannot be sterile-filtered and furthermore, since the PLGA copolymer melts at around 40° C., they cannot be heat-treated for sterility. As a result, a complex manufacturing process must all be conducted under conditions of high sterility.

The present inventors have now established that by providing a pre-formulation comprising certain amphiphilic components, at least one somatostatin analogue and a biologically tolerable solvent in a low viscosity phase, such as molecular solution, a pre-formulation may be generated addressing many of the shortfalls of previous somatostatin analogue depot formulations. In particular, the pre-formulation is easy to manufacture, may be sterile-filtered, has low viscosity (allowing easy and less painful administration typically through a narrow needle), allows a high level of bioactive agent to be incorporated (thus allowing a smaller amount of composition to be used), requires shallower injection and/or forms a desired non-lamellar depot composition in vivo having a controllable "burst" or "non-burst" release profile. The pre-formulation shows excellent storage and in vivo stability crucial for long-acting products. The compositions are also formed from materials that are non-toxic, biotolerable and biodegradable.

In a first aspect, the present invention thus provides a pre-formulation comprising a low viscosity mixture of:
a) at least one diacyl glycerol;
b) at least one phosphatidyl choline;
c) at least one oxygen containing organic solvent;
d) at least one somatostatin analogue;
wherein the pre-formulation forms, or is capable of forming, at least one liquid crystalline phase structure upon contact with an aqueous fluid.

Generally, the aqueous fluid will be a body fluid particularly extra-vascular fluid, extracellular fluid/interstitial fluid or plasma, and the pre-formulation will form a liquid crystalline phase structure when contacted with such a fluid (e.g. in vivo). The pre-formulation of the invention will generally not contain any significant quantity of water prior to administration.

In a second aspect of the invention, there is also provided a method of delivery of a somatostatin analogue to a human or non-human animal (preferably mammalian) body, this method comprising parenterally administering (e.g. i.m. or preferably s.c.) a pre-formulation comprising a low viscosity mixture of:
a) at least one diacyl glycerol;
b) at least one phosphatidyl choline;
c) at least one oxygen containing organic solvent;
d) at least one somatostatin analogue;
whereby to form at least one liquid crystalline phase structure upon contact with an aqueous fluid in vivo following administration. Preferably, the pre-formulation administered in such a method is a pre-formulation of the invention as described herein.

In a third aspect of the invention, there is also provided a method of local delivery of a somatostatin analogue to a human or non-human animal (preferably mammalian) body, this method comprising proximal administration to the disease area (e.g. intravitreal delivery for treatment of diabetic retinopathy where systemic effects are unwanted) a pre-formulation comprising a low viscosity mixture of:
a) at least one diacyl glycerol;
b) at least one phosphatidyl choline;
c) at least one oxygen containing organic solvent;
d) at least one somatostatin analogue;
whereby to form at least one liquid crystalline phase structure upon contact with an aqueous fluid in vivo following administration. Preferably, the pre-formulation administered in such a method is a pre-formulation of the invention as described herein.

In a further aspect, the present invention also provides a method for the preparation of a liquid crystalline depot composition comprising exposing a pre-formulation comprising a low viscosity mixture of:
a) at least one diacyl glycerol;
b) at least one phosphatidyl choline;
c) at least one oxygen containing organic solvent;
d) at least one somatostatin analogue;
to an aqueous fluid in vivo Preferably the pre-formulation administered is a pre-formulation of the present invention as described herein.

In a still further aspect the present invention provides a process for the formation of a pre-formulation suitable for the administration of a bioactive agent to a (preferably mammalian) subject, said process comprising forming a low viscosity mixture of a) at least one diacyl glycerol;
b) at least one phosphatidyl choline;
c) at least one oxygen containing organic solvent;
and dissolving or dispersing at least one somatostatin analogue in the low viscosity mixture, or in at least one of components a, b or c prior to forming the low viscosity mixture. Preferably the pre-formulation so-formed is a formulation of the invention as described herein.

In a yet still further aspect the present invention provides the use of a low viscosity mixture of:
a) at least one diacyl glycerol;
b) at least one phosphatidyl choline;
c) at least one oxygen containing organic solvent;
d) at least one somatostatin analogue;
in the manufacture of a pre-formulation for use in the sustained administration of said somatostatin analogue, wherein said pre-formulation is capable of forming at least one liquid crystalline phase structure upon contact with an aqueous fluid.

In a still further aspect, the present invention provides a method for the treatment of a human or non-human mammalian subject in need thereof with a somatostatin analogue, said method comprising administering to said subject a pre-formulation comprising a low-viscosity mixture of;
a) at least one diacyl glycerol;
b) at least one phosphatidyl choline;
c) at least one oxygen containing organic solvent;
d) at least one somatostatin analogue;

Preferably, the method of treatment is a method for the treatment of at least one condition selected from acromegaly, cancers (such as carcinomas and melanomas, tumours expressing at least one somatostatin receptor, sst(2)-positive tumours, sst(5)-positive tumours, prostate cancers, gastro-entero-pancreatic neuroendocrine (GEP NE) tumours and especially carcinoid tumours, insulinomas, gastrinomas, vasoactive intestinal peptide (VIP) tumours and glucagonomas), elevated growth hormone (GH), elevated insulin-like growth factor I (IGF-I), varicial bleeding (especially esophageal), chemotherapy induced gastro intestinal problems (such as diarrhea), lymphorrhea, diabetic retinopathy, thyroid eye disease, obesity, pancreatitis, and related conditions.

In a yet further aspect, the present invention provides the use of;
a) at least one diacyl glycerol;
b) at least one phosphatidyl choline;
c) at least one oxygen containing organic solvent;
d) at least one somatostatin analogue;
in the manufacture of a low viscosity pre-formulation medicament for use in the in vivo formation of a depot for treatment of acromegaly, cancer (such as carcinomas and melanomas, tumours expressing at least one somatostatin receptor, sst(2)-positive tumours, sst(5)-positive tumours, prostate cancers, gastro-entero-pancreatic neuroendocrine (GEP NE) tumours and especially carcinoid tumours, insulinomas, gastrinomas, vasoactive intestinal peptide (VIP) tumours and glucagonomas), elevated growth hormone (GH), elevated insulin-like growth factor I (IGF-I), varicial bleeding (especially espohageal), chemotherapy induced gastro intestinal problems (such as diarrhea), lymphorrhea, diabetic retinopathy, thyroid eye disease, obesity, pancreatitis, and/or related conditions The pre-formulations of the present invention are highly advantageous in that they are stable to prolonged storage in their final "administration ready" form. As a result, they may readily be supplied for administration either by health professionals or by patients or their carers, who need not be fully trained health professionals and may not have the experience or skills to make up complex preparations.

In a yet further aspect, the present invention provides a disposable administration device (which is also to include a device component) pre-loaded with a measured dose of a preformulation of the present invention. Such a device will typically contain a single dose ready for administration and will generally be sterile-packed such that the composition is stored within the device until administration. Suitable devices include cartridges, ampoules and particularly syringes and syringe barrels, either with integral needles or with standard (e.g. luer) fittings adapted to take a suitable disposable needle.

The pre-filled devices of the invention may also suitably be included in an administration kit, which kit also forms a further aspect of the invention. In a still further aspect, the invention thus provides a kit for the administration of at least one somatostatin analogue, said kit containing a measured dose of a formulation of the invention and optionally an administration device or component thereof. Preferably the dose will be held within the device or component, which will be suitable for i.m. or preferably s.c. administration. The kits may include additional administration components such as needles, swabs, etc. and will optionally and preferably contain instructions for administration. Such instructions will typically relate to administration by a route as describe herein and/or for the treatment of a disease indicated herein above.

The formulations of the present invention generate a non-lamellar liquid crystalline phase following administration. The use of non-lamellar phase structures (such as liquid crystalline phases) in the delivery of bioactive agents is now relatively well established. Such structures form when an amphiphilic compound is exposed to a solvent because the amphiphile has both polar and apolar groups which cluster to form polar and apolar regions. These regions can effectively solubilise both polar and apolar compounds. In addition, many of the structures formed by amphiphiles in polar and/or apolar solvents have a very considerable area of polar/apolar boundary at which other amphiphilic compounds can be adsorbed and stabilised. Amphiphiles can also be formulated to protect active agents, to at least some extent, from aggressive biological environments, including enzymes, and thereby provide advantageous control over active agent stability and release.

The formation of non-lamellar regions in the amphiphile/water, amphiphile/oil and amphiphile/oil/water phase diagrams is a well known phenomenon. Such phases include liquid crystalline phases such as the cubic P, cubic D, cubic G and hexagonal phases, which are fluid at the molecular level but show significant long-range order, and the $L_3$ phase which comprises a multiply interconnected bi-continuous network of bilayer sheets which are non-lamellar but lack the long-range order of the liquid crystalline phases. Depending upon their curvature of the amphiphile sheets, these phases may be described as normal (mean curvature towards the apolar region) or reversed (mean curvature towards the polar region).

The non-lamellar liquid crystalline and L3 phases are thermodynamically stable systems. That is to say, they are not simply a meta-stable state that will separate and/or reform into layers, lamellar phases or the like, but are the stable thermodynamic form of the lipid/solvent mixture.

It is important that the pre-formulations of the invention are not liquid crystalline prior to administration because bulk liquid crystalline phase is generally highly viscous. The pre-formulations are thus low viscosity, non-liquid-crystalline formulations which undergo a phase change upon administration to form a liquid crystalline mass. Particularly preferred examples of low viscosity mixtures are molecular solutions and/or isotropic phases such as L2 and/or L3 phases. As describe above, the L3 is a non-lamellar phase of interconnected sheets which has some phase structure but lacks the long-range order of a liquid crystalline phase. Unlike liquid crystalline phases, which are generally highly viscous, L3 phases are of lower viscosity. Obviously, mixtures of L3 phase and molecular solution and/or particles of L3 phase suspended in a bulk molecular solution of one or more components are also suitable. The L2 phase is the so-called "reversed micellar" phase or microemulsion. Most preferred low viscosity mixtures are molecular solutions, L3 phases and mixtures thereof. L2 phases are less preferred, except in the case of swollen $L_2$ phases as described below.

As used herein, the term "low viscosity mixture" is used to indicate a mixture which may be readily administered to a subject and in particular readily administered by means of a standard syringe and needle arrangement. This may be indicated, for example by the ability to be dispensed from a 1 ml disposable syringe through a small gauge needle. Preferably, the low viscosity mixtures can be dispensed through a needle of 19 awg, preferably smaller than 19 gauge, more preferably 23 awg (or most preferably even 27 gauge) needle by manual pressure. In a particularly preferred embodiment, the low viscosity mixture should be a mixture capable of passing through a standard sterile filtration membrane such as a 0.22 μm syringe filter. A typical range of suitable viscosities would be, for example, 0.1 to 5000 mPas, preferably 1 to 1000 mPas at 20° C.

It has been observed that by the addition of small amounts of low viscosity solvent, as indicated herein, a very significant change in viscosity can be provided. As indicated in FIG. 1, for example, the addition of only 5% solvent to a lipid mixture can reduce viscosity 100-fold and addition of 10% may reduce the viscosity up to 10,000 fold. In order to achieve this non-linear, synergistic effect, in lowering viscosity it is important that a solvent of appropriately low viscosity and suitable polarity be employed. Such solvents include those described herein infra.

The present invention provides a pre-formulation comprising components a, b, c and at least one somatostatin analogue as indicated herein. The amounts of these components will typically be in the range 40-70% a), 30-60% b) and 0.1-10% c), with the somatostatin analogue present at 0.1% to 10%. All % being by weight herein throughout, unless otherwise indicated. The formulations may consist of essentially only these components and in one aspect consist entirely of such components. Preferable ranges for component a) are 43-60%, particularly 45-55 and preferable ranges of component b) are 35-55%, particularly 40 to 50%.

Ratios of a:b are typically 40:60 to 70:30, preferably 45:55 to 60:40 and more preferably 48:52 to 55:45. Ratios of around 50:50 are highly effective.

The amount of solvent component c) in the preformulation will have a considerable effect upon several features. In particular, the viscosity and the rate (and duration) of release will alter significantly with the solvent level. The amount of solvent will thus be at least sufficient to provide a low viscosity mixture but will additionally be determined so as to provide the desired release rate. This may be determined by routine methods in view of the Examples below. Typically a level of 0.1 to 10% solvent will provide suitable release and viscosity properties. This will preferably be 2 to 8% and an amount of around 5% is highly effective.

It is the remarkable finding of the present inventors that the proportion of solvent in the formulation can be used to "tune" the release profile of the active agent during the first few days of release. In particular, although all formulations of the invention have a surprisingly low "burst/lag" effect (in fact there may be no lag period at all), and reach a plateau release level within a few days (e.g. 5 days, preferably 3 days, more preferably 1 day) of injection, if a controlled "burst"/initial release of active agent is required in the first 1-2 days then this can be provided by increasing the solvent proportion to the upper region of the range given above. In contrast, in the mid- to lower-region of the range, a formulation giving a depot with essentially no burst and a rapid decline to the plateau release level is provided.

Thus, in one embodiment, the present invention provides formulations and depots containing around 0.1 to 6 wt % component c) and having a low release of the active compound during the first days after administration ("non-burst profile"). In an alternative embodiment, the present invention provides formulations and depots containing around 6.5 to 10 wt % component c) and having high initial release of the active compound during the first days after administration ("burst profile").

The low initial release ("non-burst profile") of active agent is defined such that the area under a plasma concentration against time the curve during the first 24 hours is less than 15% of the area under the curve for the entire curve (measured or extrapolated from time 0 to infinity or from time 0 to the last sampling time point), more preferably less than 10% and most preferable less than 7%. In addition, the decline to plateau plasma concentration levels after the initial peak should be rapid, such that plateau is reached with in 48 hours, more preferably within 24 hours, and most preferably within 12 hours. Conversely, a high initial release ("burst profile") is such that more than 15% of active agent is released within 24 hours and more preferably more than 20% is released during the first 24 hours. The decline to plateau will not occur until after 36 hours, more preferably after 48 hours and most preferably after 72 hours. It is preferable that each of these profiles is combined with a rapid settling of the plasma active agent concentration to "plateau" level. For example, the plasma concentration after 10 days should be no more than 50% greater or less than the average concentration over days 5 to 20. Preferably this will be no more than 30% and more preferably no more than 20%.

As indicated above, the amount of component c in the pre-formulations of the invention will be at least sufficient to provide a low viscosity mixture (e.g. a molecular solution, see above) of components a, b and c and will be easily determined for any particular combination of components by standard methods. The phase behaviour itself may be analysed by techniques such as visual observation in combination with polarized light microscopy, nuclear magnetic resonance, and cryo-transmission electron microscopy (cryo-TEM) to look for solutions, L2 or L3 phases, or liquid crystalline phases. Viscosity may be measured directly by standard means. As described above, an appropriate practical viscosity is that which can effectively be syringed and particularly sterile filtered. This will be assessed easily as indicated herein.

Component "a" as indicated herein is at least one diacyl glycerol (DAG) and thus has two non-polar "tail" groups. The two non-polar groups may have the same or a differing number of carbon atoms and may each independently be saturated or unsaturated. Examples of non-polar groups include $C_6$-$C_{32}$ alkyl and alkenyl groups, which are typically present as the esters of long chain carboxylic acids. These are often described by reference to the number of carbon atoms and the number of unsaturations in the carbon chain. Thus, CX:Z indicates a hydrocarbon chain having X carbon atoms and Z unsaturations. Examples particularly include caproyl (C6:0), capryloyl (C8:0), capryl (C10:0), lauroyl (C12:0), myristoyl (C14:0), palmitoyl (C16:0), phytanoyl (C16:0), palmitoleoyl (C16:1), stearoyl (C18:0), oleoyl (C18:1), elaidoyl (C18:1), linoleoyl (C18:2), linolenoyl (C18:3), arachidonoyl (C20:4), behenoyl (C22:0) and lignoceroyl (C24:9) groups. Thus, typical non-polar chains are based on the fatty acids of natural ester lipids, including caproic, caprylic, capric, lauric, myristic, palmitic, phytanic, palmitolic, stearic, oleic, elaidic, linoleic, linolenic, arachidonic, behenic or lignoceric acids, or the corresponding alcohols.

Preferable non-polar chains are palmitic, stearic, oleic and linoleic acids, particularly oleic acid.

Mixtures of any number of diacyl lipids may be used as component a. Preferably this component will include at least a portion of glycerol dioleate (GDO). A highly preferred example is DAG comprising at least 50%, preferably at least 80% and even comprising substantially 100% GDO.

Since GDO and other diacyl glycerols are products derived from natural sources, there is generally a certain proportion of "contaminant" lipid having other chain lengths etc. In one aspect, GDO as used herein is thus used to indicate any commercial grade of GDO with concomitant impurities (i.e. GDO of commercial purity). These impurities may be separated and removed by purification but providing the grade is consistent this is rarely necessary. If necessary, however, "GDO" may be essentially chemically pure GDO, such as at least 80% pure, preferably at least 85% pure and more preferably at least 90% pure GDO.

Component "b" in the present invention is at least one phosphatidyl choline (PC). As with component a, this component comprises a polar head group and at least one non-polar tail group. The difference between components a and b lies principally in the polar group. The non-polar portions may thus suitably be derived from the fatty acids or corresponding alcohols considered above for component a. As with component a), the PC will contain two non-polar groups.

The phosphatidyl choline portion, even more suitably than any diacyl glycerol portion, may be derived from a natural source. Suitable sources of phospholipids include egg, heart (e.g. bovine), brain, liver (e.g. bovine) and plant sources including soybean. Such sources may provide one or more constituents of component b, which may comprise any mixture of phospholipids. Any single PC or mixture of PCs from these or other sources may be used, but mixtures comprising soy PC or egg PC are highly suitable. PC with at least 50% soy PC, more preferably at least 75% soy PC and most preferably essentially pure soy PC is preferred, although mixtures of soy & egg PC to the same proportions are also highly effective.

Since the pre-formulations of the invention are to be administered to a subject for the controlled release of a somatostatin analogue active agent, it is important that the components are biocompatible. In this regard, the preformulations of the present invention are highly advantageous since both PC and DAGs are well tolerated and are broken down in vivo into components that are naturally present in the mammalian body.

A particularly favoured combination of components a and b are GDO with PC, especially GDO with soy PC and/or egg PC.

Component "c" of the pre-formulations of the invention is an oxygen containing organic solvent. Since the pre-formulation is to generate a depot composition following administration (e.g. in vivo), upon contact with an aqueous fluid, it is desirable that this solvent be tolerable to the subject and be capable of mixing with the aqueous fluid, and/or diffusing or dissolving out of the pre-formulation into the aqueous fluid. Solvents having at least moderate water solubility are thus preferred.

In a preferred version, the solvent is such that a relatively small addition to the composition comprising a and b, i.e. preferably below 10%, give a large viscosity reductions of one order of magnitude or more. As described herein, the addition of 10% solvent can give a reduction of two, three or even four orders of magnitude in viscosity over the solvent-free composition, even if that composition is a solution or $L_2$ phase containing no solvent, or an unsuitable solvent such as water, or glycerol.

Typical solvents suitable for use as component c include at least one solvent selected from alcohols, ketones, esters (including lactones), ethers, amides and sulphoxides. Alcohols are particularly suitable and form the preferred class of solvents. Examples of suitable alcohols include ethanol, isopropanol and glycerol formal. Ethanol is most preferred. Monools are preferred to diols and polyols. Where diols or polyols are used, this is preferably in combination with an at least equal amount of monool or other preferred solvent. Examples of ketones include acetone, n-methylpyrrolidone (NMP), 2-pyrrolidone, and propylene carbonate. Suitable ethers include diethylether, glycofurol, diethylene glycol monoethyl ether, dimethylisobarbide, and polyethylene glycols. Suitable esters include ethyl acetate and isopropyl acetate and dimethyl sulphide is as suitable sulphide solvent. Suitable amides and sulphoxides include dimethylacetamide (DMA) and dimethylsulphoxide (DMSO), respectively.

A highly preferred combination is soy PC, GDO and ethanol.

It is preferable that little or none of component c contains halogen substituted hydrocarbons since these tend to have lower biocompatibility. Where a portion of halogenated solvent such as dichloromethane or chloroform is necessary, this proportion will generally be minimised.

Component c as used herein may be a single solvent or a mixture of suitable solvents but will generally be of low viscosity. This is important because one of the key aspects of the present invention is that it provides preformulations that are of low viscosity and a primary role of a suitable solvent is to reduce this viscosity. This reduction will be a combination of the effect of the lower viscosity of the solvent and the effect of the molecular interactions between solvent and lipid composition. One observation of the present inventors is that the oxygen-containing solvents of low viscosity described herein have highly advantageous and unexpected molecular interactions with the lipid parts of the composition, thereby providing a non-linear reduction in viscosity with the addition of a small volume of solvent.

The viscosity of the "low viscosity" solvent component c (single solvent or mixture) should typically be no more than 18 mPas at 20° C. This is preferably no more than 15 mPas, more preferably no more than 10 mPas and most preferably no more than 7 mPas at 20° C.

A further advantage of the present pre-formulations is that a higher level of bioactive agent may be incorporated into the system. In particular, by appropriate choice of components a-c (especially c), high levels of active agent may be dissolved or suspended in the pre-formulations. This allows a reduction in the administered volume and thus less discomfort to subjects.

The pre-formulations of the present invention typically do not contain significant amounts of water. Since it is essentially impossible to remove every trace of water from a lipid composition, this is to be taken as indicating that only such minimal trace of water exists as cannot readily be removed. Such an amount will generally be less than 1% by weight, preferably less that 0.5% by the weight of the pre-formulation. In one preferred aspect, the pre-formulations of the invention do not contain glycerol, ethylene glycol or propylene glycol and contain no more than a trace of water, as just described.

The pre-formulations of the present invention contain one or more somatostatin analogues (which are intended by any reference to "active agents" herein). Since somatostatin is a peptide hormone, typical somatostatin analogues will be peptides, especially of 14 or fewer amino acids. Preferably such peptides will be structurally constrained such as by being cyclic and/or having at least one intra-molecular crosslink. Amide, ester or particularly disulphide crosslinks are highly suitable. Preferred constrained peptides will exhibit a type-2 β turn. Such a turn is present in the key region of somatostatin. Peptides may contain only amino acids selected from those 20 α-amino acids indicated in the genetic code, or more preferably may contain their isomers and other natural and non-natural amino acids, (generally α, β or γ amino acids) and their analogues and derivatives.

The terms "somatostatin analogues", "octreotide", "lanreotide" andotheractives referred to herein evidently includes pharmaceutically acceptable salts and derivatives thereof. Typically, for example, the "octreotide" referred to herein will be the most common salt, octreotide acetate, but the free molecule, or any other biologically acceptable salt, such as hydrochloride, pamoate, citrate etc. is also encompassed by the term, unless context prohibits.

Amino acid derivatives are especially useful at the termini of the peptides, where the terminal amino or carboxylate group may be substituted by or with any other functional group such as hydroxy, alkoxy, carboxy, ester, amide, thio, amino, alkyl amino, di- or tri-alkyl amino, alkyl (by which is meant, herein throughout $C_1$-$C_{12}$ alkyl, preferably $C_1$-$C_6$ alkyl e.g. methyl, ethyl, n-propyl, isopropyl, n-butyl, iso-, sec- or t-butyl etc.), aryl (e.g phenyl, benzyl, napthyl etc) or other functional groups, preferably with at least one heteroatom and preferably having no more than 10 atoms in total, more preferably no more than 6.

Particularly preferred somatostatin analogues are constrained peptides of 6 to 10 alpha-amino acids, of which particular examples include octreotide, lanreotide (of sequence $NH_2$-(D)Naph-Cys-Tyr-(D)Trp-Lys-Val-Cys-Thr-$CONH_2$ and its cyclic derivative of sequence $NH_2$-(D)Naph-Cys-Tyr-(D)Phe-Lys-Val-Cys-Thr-$CONH_2$ both having a Cys-Cys intramolecular disulphide crosslink) and vapreotide. Most preferred is octreotide.

The somatostatin analogue will generally be formulated as 0.1 to 10% by weight of the total formulation. Typical values will be 1 to 8%, preferably 2 to 6% and more preferably 2.5 to 5%. A somatostatin analogue content of around 3% is most preferable.

Doses of the somatostatin analogue suitable for inclusion in the formulation, and thus the volume of formulation used will depend upon the release rate (as controlled, for example by the solvent type and amount use) and release duration, as well as the desired therapeutic level, the activity and the rate of clearance of the particular active chosen. Typically an amount of 1 to 1000 mg (e.g. 1 to 500 mg) per dose would be suitable for providing a therapeutic level for between 7 and 180 (e.g. between 7 and 90 days). This will preferably be 5 to 300 mg. For octreotide, the level will typically be around 10 to 180 mg (e.g. for a 30 to 90 day duration). Preferably, the amount of octreotide will be around 0.2 to 3 mg per day between injections. Thus a depot administered every 30 days would have 6 to 90 mg or a 90 day depot have 18 to 270 mg of octreotide. In some situations, especially where advanced tumours are present, a high dose equivalent to around 40 to 160 mg octreotide per week of duration (e.g. 160 to 640 mg for a 4-week depot) will be suitable. Such depots will typically be formulated for administration once every 2-8 weeks, preferably once every 4-6 weeks.

The pre-formulations of the present invention are formulated to be administered parenterally. This administration will generally not be an intra-vascular method but will preferably be subcutaneous, intraocular (e.g. intra-vitreal or subconjunctival) or intramuscular. Typically the administration will be by injection, which term is used herein to indicate any method in which the formulation is passed through the skin, such as by needle, catheter or needle-less injector.

Preferred parenteral administration is by i.m or s.c. injection, most preferably by deep s.c. injection. This has the advantage of being less deep and less painful to the subject than the (deep) i.m. injection used for current octreotide depots and is technically most suitable in the present case as it combines ease of injection with low risk of skin side effects.

The pre-formulations of the present invention provide non-lamellar liquid crystalline depot compositions upon exposure to aqueous fluids, especially in vivo. As used herein, the term "non-lamellar" is used to indicate a normal or reversed liquid crystalline phase (such as a cubic or hexagonal phase) or the L3 phase or any combination thereof. The term liquid crystalline indicates all hexagonal, all cubic liquid crystalline phases and/or all mixtures thereof. Hexagonal as used herein indicates "normal" or "reversed" hexagonal (preferably reversed) and "cubic" indicates any cubic liquid crystalline phase unless specified otherwise.

For many combinations of lipids, only certain non-lamellar phases exist, or exist in any stable state. It is a surprising feature of the present invention that compositions as described herein frequently exhibit non-lamellar phases which are not present with many other combinations of components. In one particularly advantageous embodiment, therefore, the present invention relates to compositions having a combination of components for which an $I_2$ and/or $L_2$ phase region exists when diluted with aqueous solvent. The presence or absence of such regions can be tested easily for any particular combination by simple dilution of the composition with aqueous solvent and study of the resulting phase structures by the methods described herein.

In a highly advantageous embodiment, the compositions of the invention may form an $I_2$ phase, or a mixed phase including $I_2$ phase upon contact with water. The $I_2$ phase is a reversed cubic liquid crystalline phase having discontinuous aqueous regions. This phase is of particular advantage in the controlled release of active agents and especially in combination with polar active agents, such as water soluble actives because the discontinuous polar domains prevent rapid diffusion of the actives. Depot precursors in the $L_2$ are highly effective in combination with an $I_2$ phase depot formation. This is because the $L_2$ phase is a so-called "reversed micellar" phase having a continuous hydrophobic region surrounding discrete polar cores. $L_2$ thus has similar advantages with hydrophilic actives.

In transient stages after contact with body fluid the composition can comprise multiple phases since the formation of an initial surface phase will retard the passage of solvent into the core of the depot, especially with substantial sized administrations of internal depots. Without being bound by theory, it is believed that this transient formation of a surface phase, especially a liquid crystalline surface phase, serves to dramatically reduce the "burst/lag" profile of the present compositions by immediately restricting the rate of exchange between the composition and the surroundings. Transient phases may include (generally in order from the outside towards the centre of the depot): $H_{II}$, or $L_\alpha$, $I_2$, $L_2$, and liquid (solution). It is highly preferred that the composition of the invention is capable forming at least two and more preferably at least three of these phases simultaneously at transient stages after contact with water at physiological temperatures. In particular, it is highly preferred that one of the phases formed, at least transiently, is the $I_2$ phase.

It is important to appreciate that the preformulations of the present invention are of low viscosity. As a result, these preformulations must not be in any bulk liquid crystalline phase since all liquid crystalline phases have a viscosity significantly higher than could be administered by syringe or spray dispenser. The preformulations of the present invention will thus be in a non-liquid crystalline state, such as a solution, $L_2$ or $L_3$ phase, particularly solution or $L_2$. The $L_2$ phase as used herein throughout is preferably a "swollen" $L_2$ phase containing greater than 10 wt % of solvent (component c) having a viscosity reducing effect. This is in contrast to a "concentrated" or "unswollen" $L_2$ phase containing no solvent, or a lesser amount of solvent, or containing a solvent (or mixture) which does not provide the decrease in viscosity associated with the oxygen-containing, low viscosity solvents specified herein.

Upon administration, the pre-formulations of the present invention undergo a phase structure transition from a low viscosity mixture to a high viscosity (generally tissue adherent) depot composition. Generally this will be a transition from a molecular mixture, swollen $L_2$ and/or L3 phase to one or more (high viscosity) liquid crystalline phases such as normal or reversed hexagonal or cubic liquid crystalline phases or mixtures thereof. As indicated above, further phase transitions may also take place following administration. Obviously, complete phase transition is not necessary for the functioning of the invention but at least a surface layer of the administered mixture will form a liquid crystalline structure. Generally this transition will be rapid for at least the surface region of the administered formulation (that part in direct contact with air, body surfaces and/or body fluids). This will most preferably be over a few seconds or minutes (e.g. up to 30 minutes, preferably up to 10 minutes, more preferably 5 minutes of less). The remainder of the composition may change phase to a liquid crystalline phase more slowly by diffusion and/or as the surface region disperses.

In one preferred embodiment, the present invention thus provides a pre-formulation as described herein of which at least a portion forms a hexagonal liquid crystalline phase upon contact with an aqueous fluid. The thus-formed hexagonal phase may gradually disperse and/or degrade, releasing the active agent, or may subsequently convert to a cubic liquid crystalline phase, which in turn then gradually disperses. It is believed that the hexagonal phase will provide a more rapid release of active agent, in particular of hydrophilic active agent, than the cubic phase structure, especially the $I_2$ and $L_2$ phase. Thus, where the hexagonal phase forms prior to the cubic phase, this will result in an initial release of active agent to bring the concentration up to an effective level rapidly, followed by the gradual release of a "maintenance dose" as the cubic phase degrades. In this way, the release profile may be controlled.

Without being bound by theory, it is believed that upon exposure (e.g. to body fluids), the pre-formulations of the invention lose some or all of the organic solvent included therein (e.g. by diffusion) and take in aqueous fluid from the bodily environment (e.g. the in vivo environment) such that at least a part of the formulation generates a non-lamellar, particularly liquid crystalline phase structure. In most cases these non-lamellar structures are highly viscous and are not easily dissolved or dispersed into the in vivo environment. The result is a monolithic "depot" generate in vivo with only a limited area of exposure to body fluids. Furthermore, because the non-lamellar structure has large polar, apolar and boundary regions, it is highly effective in solubilising and stabilising active agents such as peptides and protecting these from degradation mechanisms. As the depot composition formed from the pre-formulation gradually degrades over a period of days, weeks or months, the active agent is gradually released and/or diffuses out from the composition. Since the environment within the depot composition is relatively protected, the pre-formulations of the invention are highly suitable for active agents with a relatively low biological half-life (see above).

The depot systems formed by the formulations of the present invention are highly effective in protecting the active agent from degradation and thus allow an extended release period. Comparative tests have been carried out between the known PLGA slow-release product and formulations of the present invention containing GDO, soy PC, ethanol and octreotide. These indicate that formulations of the present invention give lesser degradation under simulated in vivo conditions than known compositions of octreotide with PLGA microspheres. The formulations of the invention thus may provide in vivo depots of somatostatin analogues which require administration only once every 20 to 90 days, preferably 30 to 60 days, more preferably 35 to 48 days. Evidently, a longer stable release period is desirable for patient comfort and compliance as well as demanding less time from health professionals.

A considerable advantage of the depot precursors of the present invention is that they are stable homogeneous phases. That is to say, they may be stored for considerable periods (preferably at least 6 months) without phase separation. As well as providing advantageous storage, this allows for the dose of somatostatin analogue to be selected by reference to the species, age, sex, weight, and/or physical condition of the individual subject, by means of injecting a selected volume.

Furthermore, the present inventors have surprisingly found that the initial release of active agent (observed as $C_{max}$) is not proportional to dose volume, in ranges of at least 10-fold in sample volume injection (see examples and figures below), while the total drug exposure (observed as AUC or mean plateau plasma concentration) is proportional to the injection volume. On the contrary, it has been shown that $C_{max}$ can be correlated to the surface area of the injected dose volume. That is, $C_{max}$ is proportional to the two-third power of the injected dose volume. Increasing the dose volume by a factor of 10 will not increase the $C_{max}$ 10 times and the relationship between $C_{max}$ and the total drug exposure (AUC or mean plateau plasma concentration level) will thus decrease with increasing dose volume. This is highly advantageous, because this property reduces the risk of reaching potentially toxic plasma drug concentrations, even if the total dose is significantly increased. It also allows a degree of independent control to be exerted over the plateau concentration and the peak concentration by varying the concentration of active in the formulation and the injected volume. Even in situations where dosing is not directly proportional to injection volume, however, the homogenous nature of the depot precursors importantly allow for partial administration of a pre-measured dose and this administration may be made by reference to a dosing table, chart, software calculation etc. which may take into account any or all relevant subject variables.

The present invention thus provides for methods comprising the selection of a dosing amount specific to an individual, particularly by subject weight or body surface area. The means for this dose selection being by administration volume.

It is an unexpected finding of the present inventors that the pre-formulations result in a depot composition that have very little "burst" effect in the active agent release profile. This is unexpected because it might be expected that the low viscosity mixture (especially if this is a solution) of the pre-composition would rapidly lose active agent upon exposure to water. In fact, pre-formulations of the invention have shown considerably less of an initial "burst" than previously known polymer-base depot compositions which tend to have an initial "wash off" of surface-bound active agent. This is illustrated in the Examples below and Figures attached hereto. In one embodiment, the invention thus provides injectable preformulations and resulting depot compositions wherein the highest plasma concentration of active after administration is no more than 10 times the average concentration between 24 hours and 5 days of administration. This ratio is preferably no more than 8 times and most preferably no more than 5 times the average concentration.

The compositions if the invention also allow for the generation of depot compositions with very little "lag" effect after administration. In a further embodiment, the invention thus provides injectable preformulations and resulting depot compositions wherein the plasma concentration of active at 7 days after a single administration is no lower than the plasma concentration of active at 21 days after administration. Similarly, the concentration of active should be higher at all times in the first 21 days than the concentration at any time from 30 days after administration onwards. This gradually decaying release profile has not previously been demonstrated for a somatostatin analogue formulation.

A further and considerable advantage of the depot compositions formed by the preformulations of the present invention over PLGA based depots is that the compositions of the invention produce less injury at the site of injection. PLGA is a biodegradable polymer which generates lactic and glycolic acids upon breakdown and so releases these irritant by-products over the entire duration of active agent release (and potentially longer). This results in "capsule" formation and the generation of scar tissue which may remain for long periods after administration. In contrast, the compositions of the present invention generate no acid byproducts and generally cause only minor, reversible effects at the injection site. This has been clearly observed in animals by visual inspection at necroscopy. Most signs of the depot have disappeared, for example, 8-12 weeks after i.m or s.c. injection. Furthermore, because of the non-irritant nature of the formulations, application directly to the eyes is possible and has been observed to cause no irritation in a rabbit model.

The following are particular examples of octreotide formulations. In one embodiment of the invention, the pre-formulations as such are not one of those listed in the table below. In alternative embodiments, these constitute highly preferred examples of compositions of and for use in aspects of the invention, particularly in pre-filled articles, kits, methods of medical treatment and the use of compositions in the manufacture of a medicament.

TABLE 1

Weight Ratios:

| Formulation | OCT | EtOH | PC | GDO |
|---|---|---|---|---|
| X1 | 2.4 | 10 | 36 | 54 |
| X2 | 6 | 10 | 36 | 54 |
| X3 | 0.5 | 10 | 36 | 54 |

TABLE 2

Weight %

| Formulation | OCT | EtOH | PC | GDO1 | GDO2 | GDO3 | TP | DOPG |
|---|---|---|---|---|---|---|---|---|
| E | 2 | 10 | 35.2 | — | — | 52.8 | — | — |
| F | 2 | 10 | 35.2 | 52.8 | — | — | — | — |
| G | 2 | 10 | 35.2 | — | 52.8 | — | — | — |
| H | 2 | 10 | 26.4 | — | — | — | 61.6 | — |
| I | 1 | 10 | 35.6 | 53.4 | — | — | — | — |
| J | 2 | 5 | 37.2 | — | — | 55.8 | — | — |
| K | 3 | 5 | 36.8 | — | — | 55.2 | — | — |
| L | 6 | 5 | 35.6 | — | — | 53.5 | — | — |
| M | 3 | 5 | 35.8 | — | — | 55.2 | — | 1 |
| N | 3 | 5 | 33.8 | — | — | 55.2 | — | 3 |
| O | 3 | 5 | 30.8 | — | — | 55.2 | — | 6 |
| P | 3 | 5 | 46 | — | — | 46 | — | — |
| Q | 3 | 10 | 43.5 | — | — | 43.5 | — | — |
| R | 6 | 10 | 42 | — | — | 42 | — | — |
| S | 3 | 7 | 45 | — | — | 45 | — | — |
| T | 6 | 7 | 43.5 | — | — | 43.5 | — | — | where OCT is octreotide, EtOH is ethanol, PC is LIPOID S100 soybean phosphatidylcholine, GDO is glycerol dioleate, TP is α-tocopherol, DOPG is dioleoyl phosphatidylglycerol GDO quality (according to AC)

| | Monoglycerides | Diglycerides | Triglycerides |
|---|---|---|---|
| GDO1 | 10.9% | 87.5% | 1.4% |
| GDO2 | 4.2% | 92.1% | 3.5% |
| GDO3 | 0.5% | 95.3% | 4.0% |

In combination with the features and preferred features indicated herein, the preformulations of the invention may have one or more of the following preferred features independently or in combination:

They are not formulations as indicated in Tables 1 or 2;
They are compositions as indicated in Tables 1 or 2;
Component a) comprises, consists essentially of or preferably consists of GDO;
Component b) comprises, consists essentially of or preferably consists of soy PC;
Component c) comprises, consists essentially of or preferably consists of a 1, 2, 3 or 4 carbon alcohol, preferably isopropanol or more preferably ethanol;
The preformulation contains at least one somatostatin analogue selected from those indicated herein, preferably octreotide, lanreotide or vapreotide;
The preformulation has a low viscosity as indicated herein.
The preformulation forms a liquid crystalline phase as indicated herein upon in vivo administration.
The preformulation generates a depot following in vivo administration, which depot releases at least one somatostatin analogue at a therapeutic level over a period of at least 30 days, preferably at least 40 days, more preferably at least 60 days.

In combination with the features and preferred features indicated herein, the method(s) of treatment of the present invention may have one or more of the following preferred features independently or in combination:

The method comprises the administration of at least one formulation as indicated in tables 1 or 2;
The method comprises the administration of at least one formulation with one or more preferred features as indicated above;
The method comprises the administration of at least one formulation as indicated herein by i.m., s.c. or preferably deep s.c. injection;
The method comprises administration by means of a pre-filled administration device as indicated herein;
The method comprises administration through a needle no larger than 19 gauge, preferably smaller than 19 gauge, more preferably 23 gauge;
The method comprises a single administration every 20 to 90 days, preferably 30 to 60 days, more preferably 35 to 48 days.

In combination with the features and preferred features indicated herein, the use(s) of the preformulations indicated herein in the manufacture of medicaments may have one or more of the following preferred features independently or in combination:

The use comprises the use of at least one formulation as indicated in tables 1 or 2;
The use comprises the use of at least one formulation with one or more preferred features as indicated above;
The use comprises the manufacture of a medicament for administration of at least one formulation as indicated herein by i.m., s.c. or preferably deep s.c. injection;
The use comprises the manufacture of a medicament for administration by means of a pre-filled administration device as indicated herein;
The use comprises the manufacture of a medicament for administration through a needle no larger than 19 gauge, preferably smaller than 19 gauge, more preferably 23 gauge or smaller;

The use comprises the manufacture of a medicament for administration once every 20 to 90 days, preferably 30 to 60 days, more preferably 35 to 48 days.

In combination with the features and preferred features indicated herein, the pre filled devices of the invention may have one or more of the following preferred features independently or in combination:

They contain least one formulation as indicated in tables 1 or 2;
They contain a preferred formulation as indicated herein;
They comprise a needle smaller than 19 gauge, preferably no larger than 23 gauge;
They contain a single dose of 1 to 500 mg of somatostatin analogue, preferably 5 to 300 mg;
They contain octreotide, at around 10 to 180 mg;
They contain octreotide at around 0.2 to 3 mg per day between scheduled administrations;
They contain a total volume for administration of no more than 5 ml, preferably no more than 3 ml more preferably no more than 2 ml.

In combination with the features and preferred features indicated herein, the kits of the invention may have one or more of the following preferred features independently or in combination:

They contain least one formulation as indicated in tables 1 or 2;
They contain a preferred formulation as indicated herein;
They contain a prefilled device as indicated herein;
They contain a needle no larger than 19 gauge, preferably no larger than 23 gauge;
They contain a single dose of 1 to 500 mg of somatostatin analogue, preferably 5 to 300 mg;
They contain octreotide, at around 10 to 180 mg;
They contain octreotide at around 0.2 to 3 mg per day between scheduled administrations;
They contain a total volume for administration of no more than 5 ml, preferably no more than 3 ml more preferably no more than 2 ml.
They contain instructions for administration by a route and/or at a frequency as indicated herein;
They contain instructions for administration for use in a method of treatment as described herein.

The Invention will now be further illustrated by reference to the following non-limiting Examples and the attached Figures, in which;

FIG. 1 demonstrates the non-linear decrease of pre-formulation viscosity upon addition of N-methylpyrrolidinone (NMP) and EtOH;

Figure 7:
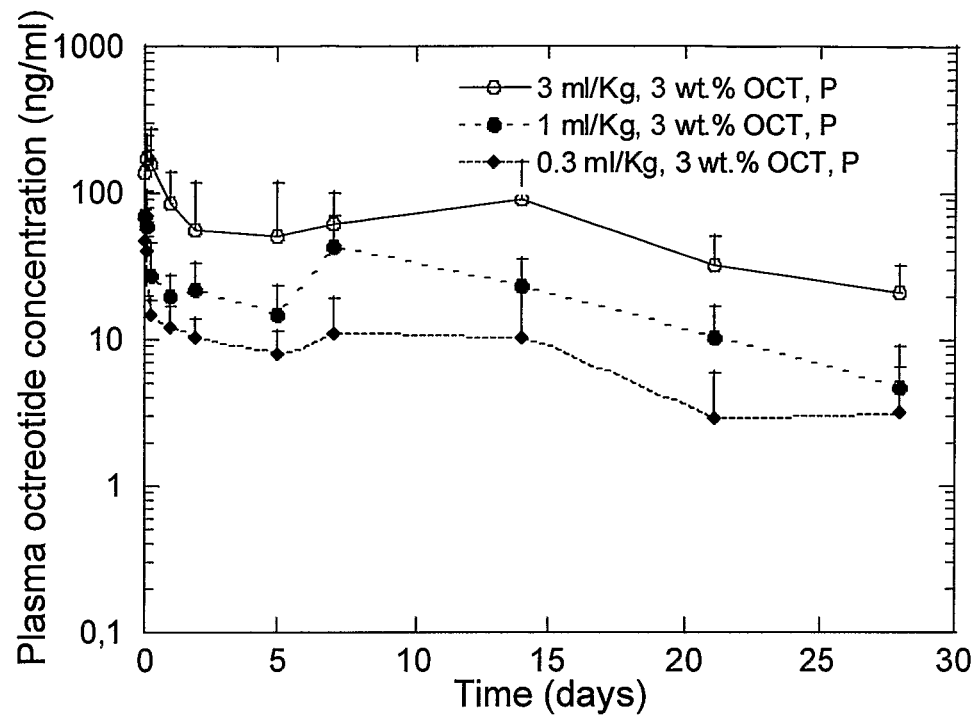
Figure 8:
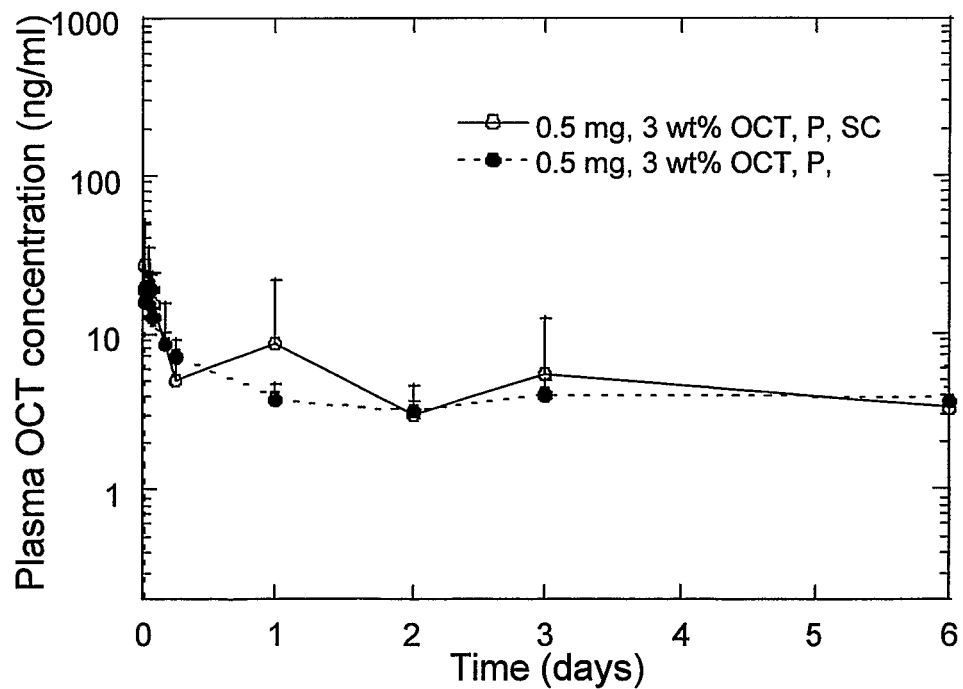

FIG. 7 shows plasma octreotide over time in rats after s.c. dosing of 9, 30, and 90 mg/kg octreotide in 0.3, 1, and 3 ml/kg of the P formulation; and FIG. 8 shows plasma octreotide concentration over 6 days in dogs after s.c. and i.m dosing of 0.5 mg formulation P.

EXAMPLES

Example 1

Availability of Various Liquid Crystalline Phases in the Depot by Choice of Composition Injectable formulations containing different proportions of phosphatidyl choline ("PC"-Epikuron 200) and glycerol dioleate (GDO) and with EtOH as solvent were prepared to illustrate that various liquid crystalline phases can be accessed after equilibrating the depot precursor formulation with excess water.

Appropriate amounts of PC and EtOH were weighed in glass vials and the mixture was placed on a shaker until the PC completely dissolved to form a clear liquid solution. GDO was then added to form an injectable homogenous solution.

Each formulation was injected in a vial and equilibrated with excess water. The phase behaviour was evaluated visually and between crossed polarizes at 25° C. Results are presented in the Table below:

| Formulation | PC (wt %) | GDO (wt %) | EtOH (wt %) | Phase in $H_2O$ |
| --- | --- | --- | --- | --- |
| A | 22.5 | 67.5 | 10.0 | $L_2$ |
| B | 28.8 | 61.2 | 10.0 | $I_2$ |
| C | 45.0 | 45.0 | 10.0 | $H_{II}$ |
| D | 63.0 | 27.0 | 10.0 | $H_{II}/L_\alpha$ |

$L_2$ = reversed micellar phase
$I_2$ = reversed cubic liquid crystalline phase
$H_{II}$ = reversed hexagonal liquid crystalline phase
$L_\alpha$ = lamellar phase Example 2

Viscosity in PC/GDO (6:4) or PC/GDO (3:7) on Addition of Solvent (EtOH, PG and NMP)

A mixture of PC/GDO/EtOH was manufactured according to the method in Example 1. All, or nearly all, of the EtOH was removed from the mixture with a rotary evaporator (vacuum, 40° C., 1 h) and the resulting solid mixture were weighed in glass vial after which 2, 5, 10 or 20% of a solvent (EtOH, propylene glycol (PG) or n-methylpyrrolidone (NMP)) was added. The samples were allowed to equilibrate several days before the viscosity was measured at a shear rate of 0.1 $s^{-1}$ with a Physica UDS 200 rheometer at 25° C.

Figure 1:
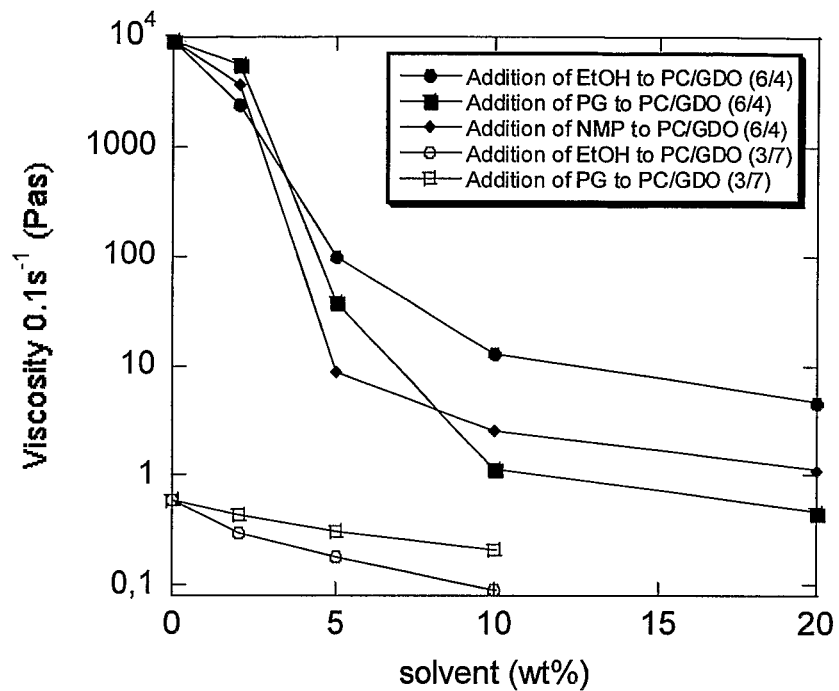

This example clearly illustrates the need for solvent with certain depot precursors in order to obtain an injectable formulation (see FIG. 1). The viscosity of solvent-free PC/GDO mixtures increases with increasing ratio of PC. Systems with low PC/GDO ratio (more GDO) are injectable with a lower concentration of solvent.

Example 3

Preparation of Depot Composition Containing the Peptide Octreotide

Octreotide is a synthetic octa-peptide, typically provided as an acetate salt, and is similar to the hormone somatostatin.

Octreotide decreases production of substances such as growth hormone, insulin and glucagons. It is used in treatment of acromegaly, and to reduce flushing and watery diarrhea caused by metastatic cancerous tumours (carcinoid syndrome) or tumours called vasoactive intestinal peptide tumours (VIPomas).

24 mg or 60 mg octreotide was dissolved in 0.1 g EtOH. 0.36 g PC and 0.54 g GDO were subsequently dissolved in this solution and a depot formulation precursor was obtained. Injecting the formulation precursor into excess aqueous phase (syringe 23 G; 0.6 mm×30 mm) resulted in a monolithic liquid crystalline phase ($I_2$ structure). I.e. octreotide (2.4% or 6.0%) did not change monolith formation and phase behaviour after exposure to an aqueous environment.

The octreotide depot precursor formulations in this Example were tested for stability against crystallization during storage. Each formulation was stable at 4-8° C. for at least two weeks.

Example 4

In Vivo Release Study from Depot Formulation Containing Octreotide Subcutaneously Administered In an in vivo rat model the drug release of octreotide was followed during 28 days. The rats were surgically prepared by insertion of a silicon catheter into the jugular vein. To days after surgery, the formulations were administered subcutaneously in the dorsal region, slightly posterior to the scapulae by using a syringe (23 G, 0.6 mm×25 mm). The octreotide dose was 10 mg/kg and volume 1 ml/kg corresponding to a drug load of 1% octreotide in the depot formulation precursor (PC/GDO/EtOH (36/54/10)). Blood samples were collected through the catheter for a period of 28 days (see FIG. 2) and stabilized with EDTA. Aprotinin (500 KIE/ml blood), a protease inhibitor, were added to the samples to prevent enzymatic degradation of the octreotide during processing. The octreotide concentration in the rat plasma was determined using an enzyme-linked immunosorbent assay (ELISA).

Figure 2:
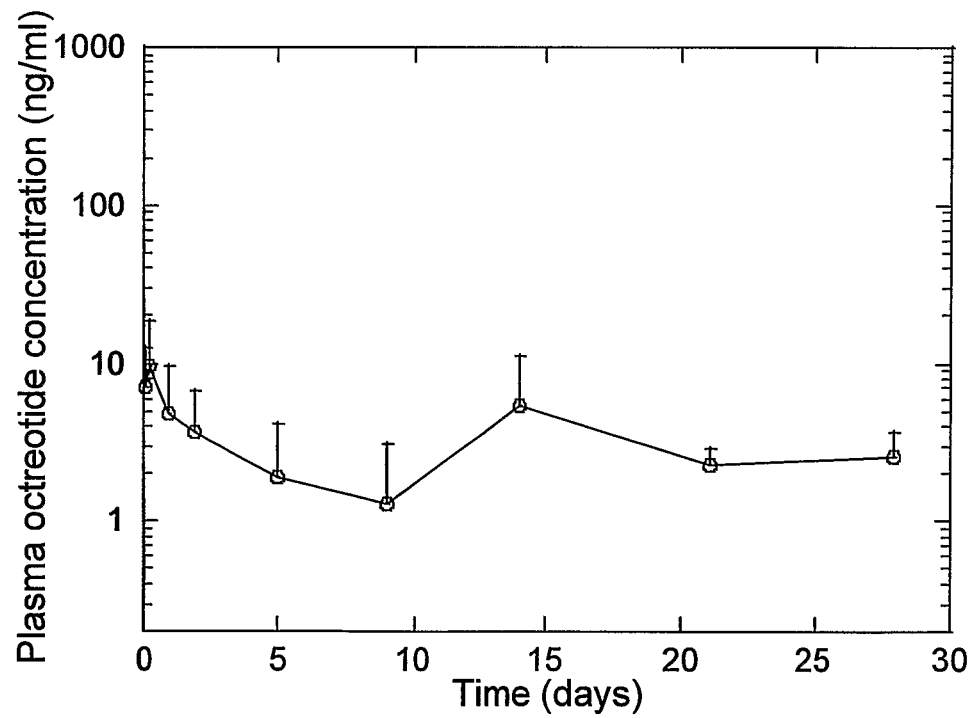
FIG. 2 shows the plasma concentration (in rats) of octreotide (OCT) over 28 days following subcutaneous injection of a depot formulation comprising PC/GDO/EtOH (36/54/10 wt %) containing 5 mg OCT/g formulation, corresponding to 0.5% drug load.

From FIG. 2 it appears that the investigated formulation gives a release profile essentially without a burst effect (less than 10% OCT is released within 24 hours).

FIG. 2 thus shows plasma octreotide over time in rats (n=3) after s.c. dosing of 10 mg/kg octreotide (1% drug load) in 1 ml/kg of the depot formulation precursor (PC/GDO/EtOH (36/54/10).

Plasma octreotide concentration rapidly reached its maximum, where after the plasma levels slowly decreased to reach a plateau level within a few days. The "burst" (initial release over the first 24 hours) was <10%. Data is presented as means±standard deviation.

Example 5

Degradation of Depot Formulation in the Rat

Various volumes (1, 2, 6 ml/kg) of the depot precursor (36% wt PC, 54% wt GDO, and 10% wt EtOH) were injected in the rat and the size of the depot was measured in two perpendicular directions with a slide-caliper over a period of 14 days. The size of the depot was estimated as the size corrected for the thickness of the skin. The baseline size was determined on day 3 after injection, after having allowed the formulation and subcutaneous tissue to stabilize. It was found that the mean diameter of the depot was reduced by approximately 20% over 14 days and that substantial amounts of the formulations were still present subcutaneously in the rat after this time, see Table Mean diameter of depot monolith.

| Dose (ml/kg) | Mean diameter day 3 (mm) | Mean diameter day 14 (mm) |
|---|---|---|
| 1 (n = 3) | 15.8 | 12.5 |
| 2 (n = 3) | 18.5 | 15.3 |
| 6 (n = 3) | 23.3 | 19.3 |

Example 6

Further Examples of Viscosity in PC/GDO Mixtures on Addition of Co-Solvent

Mixtures of PC/GDO and co-solvent were prepared according to the methods of Example 1 and Example 2 in the proportions indicated in the table below. The samples were allowed to equilibrate for several days before viscosity measurements were performed using a Physica UDS 200 rheometer at 25° C.

| Sample | PC/GDO (wt/wt) | EtOH/ wt % | Glycerol/ wt % | $H_2O$/ wt % | Viscosity/ mPas |
|---|---|---|---|---|---|
| 1 | 50/50 | 3 | — | — | 1900 |
| 2 | 50/50 | 5 | — | — | 780 |
| 3 | 50/50 | 7 | — | — | 430 |
| 4 | 50/50 | 8 | — | — | 300 |
| 5 | 50/50 | 10 | — | — | 210 |
| 6 | 50/50 | 15 | — | — | 100 |
| 7 | 45/55 | 3 | — | — | 1350 |
| 8 | 45/55 | 5 | — | — | 540 |
| 9 | 45/55 | 7 | — | — | 320 |
| 10 | 45/55 | 8 | — | — | 250 |
| 11 | 45/55 | 10 | — | — | 150 |
| 12 | 45/55 | 15 | — | — | 85 |
| 13 | 40/60 | 3 | — | — | 740 |
| 14 | 40/60 | 5 | — | — | 400 |
| 15 | 40/60 | 7 | — | — | 240 |
| 16 | 40/60 | 8 | — | — | 200 |
| 17 | 40/60 | 10 | — | — | 130 |
| 18 | 40/60 | 15 | — | — | 57 |
| 19 | 40/60 | — | 10 | — | $8 * 10^6$ |
| 20 | 40/60 | — | — | 3 | $2.5 * 10^8$ |
| 21 | 40/60 | — | — | 5 | $4 * 10^7$ |

This example further illustrates the need for a solvent with viscosity lowering properties in order to obtain injectable formulations. The mixtures containing glycerol (sample 19) or water (samples 20 and 21) are too viscous to be injectable at solvent concentrations equivalent to the samples containing EtOH (compare with samples 13, 14 and 17).

Example 7

Octreotide Formulation Compositions

Formulations were prepared as in Example 1 by mixing the peptide active octreotide with a mixture of GDO (at one of several purity levels) or tocopherol, PC, ethanol and optionally dioleoyl PG in the following proportions (by weight)

| Formulation | OCT | EtOH | PC | GDO1 | GDO2 | GDO3 | TP | DOPG |
|---|---|---|---|---|---|---|---|---|
| E | 2 | 10 | 35.2 | — | — | 52.8 | — | — |
| F | 2 | 10 | 35.2 | 52.8 | — | — | — | — |
| G | 2 | 10 | 35.2 | — | 52.8 | — | — | — |
| H | 2 | 10 | 26.4 | — | — | — | 61.6 | — |
| I | 1 | 10 | 35.6 | 53.4 | — | — | — | — |
| J | 2 | 5 | 37.2 | — | — | 55.8 | — | — |
| K | 3 | 5 | 36.8 | — | — | 55.2 | — | — |
| L | 6 | 5 | 35.6 | — | — | 53.5 | — | — |
| M | 3 | 5 | 35.8 | — | — | 55.2 | — | 1 |
| N | 3 | 5 | 33.8 | — | — | 55.2 | — | 3 |
| O | 3 | 5 | 30.8 | — | — | 55.2 | — | 6 |
| P | 3 | 5 | 46 | — | — | 46 | — | — |
| Q | 3 | 10 | 43.5 | — | — | 43.5 | — | — |
| R | 6 | 10 | 42 | — | — | 42 | — | — |
| S | 3 | 7 | 45 | — | — | 45 | — | — |
| T | 6 | 7 | 43.5 | — | — | 43.5 | — | — | where OCT is octreotide acetate, EtOH is ethanol, PC is LIPOID S100 soybean phosphatidylcholine, GDO is glycerol dioleate, TP is α-tocopherol, DOPG is dioleoyl phosphatidylglycerol

| Formulation | OCT | EtOH | PC | GDO3 |
|---|---|---|---|---|
| U | 3.5 | 5 | 45.75 | 45.75 |
| V | 4.68 | 5 | 45.16 | 45.16 |
| X | 5 | 5 | 45 | 45 |
| Y | 5.84 | 5 | 44.58 | 44.58 | where OCT is octreotide acetate, EtOH is ethanol, PC is LIPOID S100 soybean phosphatidylcholine, GDO is glycerol dioleate

| Formulation | OCT | EtOH | PC | GDO3 |
|---|---|---|---|---|
| Z | 3.5 | 5 | 45.75 | 45.75 |
| AA | 4.68 | 5 | 45.16 | 45.16 |
| BB | 5 | 5 | 45 | 45 |
| CC | 5.84 | 5 | 44.58 | 44.58 | where OCT is octreotide acetate, EtOH is ethanol, PC is LIPOID E80 Egg-phosphatidylcholine, GDO is glycerol dioleate

| | GDO quality (according to AC) | | |
|---|---|---|---|
| | Monoglycerides | Diglycerides | Triglycerides |
| GDO1 | 10.9% | 87.5% | 1.4% |
| GDO2 | 4.2% | 92.1% | 3.5% |
| GDO3 | 0.5% | 95.3% | 4.0% |

Formulation P (for composition see above) was administered by s.c. injection in the rat at a level of 1 ml formulation per kg body weight, corresponding to 30 mg/kg of octreotide.

Octreotide plasma levels after administration were monitored for 5 days to examine any burst profile. It was observed that the highest plasma concentration was less than three fold greater than the average plasma concentration over the first 5 days.

Figure 3:
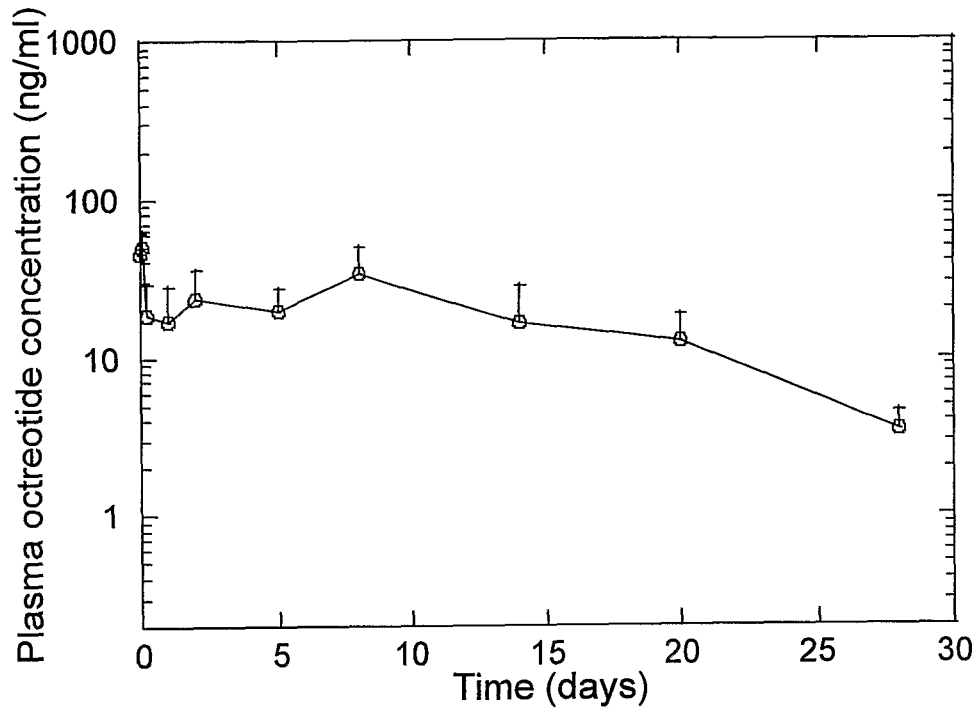
FIG. 3 shows the plasma concentration (in rats) of octreotide (OCT) over 5 days following subcutaneous injection of a depot formulation comprising PC/GDO/EtOH (47.5/47.5/5.0 wt %) containing 30 mg OCT/g formulation, corresponding to 3% drug load.

The results of the study are shown in FIG. 3

Example 8

A 6 Week Study of Octreotide Depot in Dogs

The objective of this study was to assess the basal pharmacokinetic data of octreotide. Preformulation P as described in Example 7 was used.

The study was performed in 3 male and 3 female beagle dogs (around 5 months old). The dogs were dosed s.c. in the neck m with the formulation containing octreotide (0.5 mL dosing volume, 30 mg octreotide per mL).

Blood was collected from the bijugular trunk for analysis during 42 days (totally 20 samples) and stabilized with EDTA. Aprotinin (500 KIE/mL blood) was added to the samples to prevent degradation of the octreotide during processing.

Figure 4:
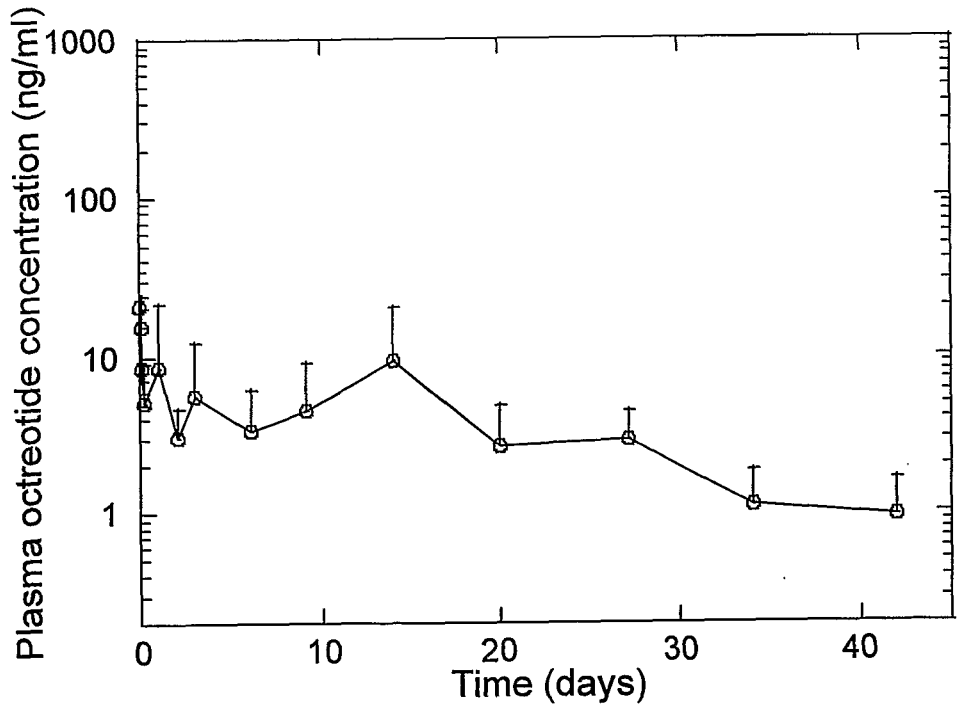
FIG. 4 shows plasma octreotide over time in beagle dogs after s.c. dosing of 15 mg (approx. 1.7 mg/kg) octreotide (3% drug load) in 0.5 ml of the P depot formulation precursor (PC/GDO/EtOH (47.5/47.5/5).
Figure 5:
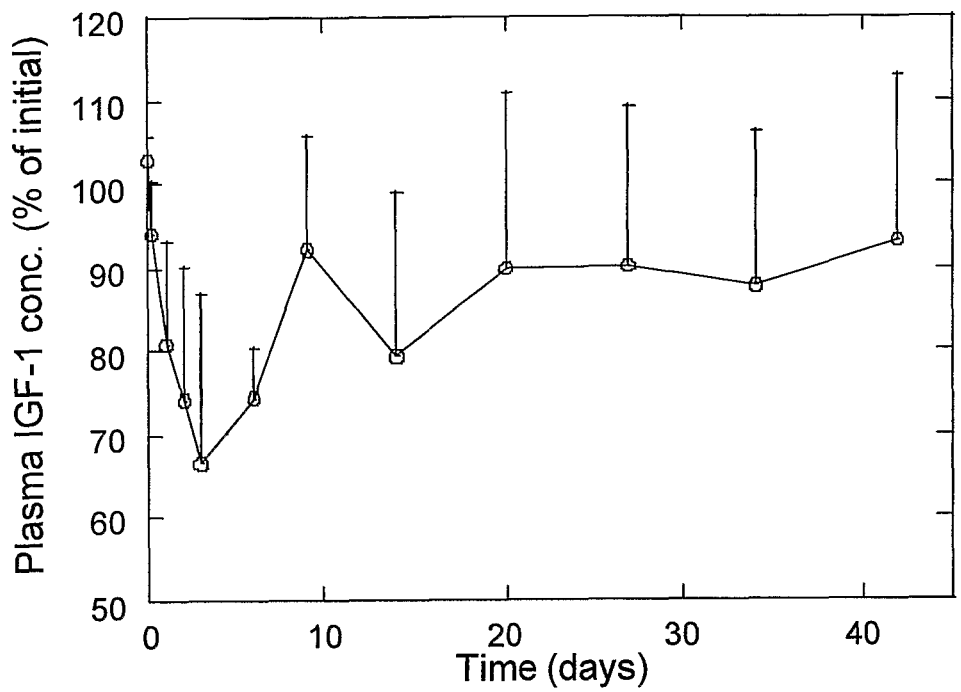
FIG. 5 shows plasma IGF-1 concentration as % of baseline over time in beagle dogs after s.c. dosing of 15 mg (approx. 1.7 mg/kg) octreotide (3% drug load) in 0.5 ml of the P depot formulation precursor.

The plasma levels of Octreotide (OCT) and of Insulin like growth factor 1 (IGF-1), were measured at each time point using enzyme-linked immunosorbent assay (ELISA) methods and the results are shown in FIGS. 4 and 5. It was observed that octreotide levels remained above the 1 ng/ml level up to the 42 day termination of the study indicating a potentially therapeutic dose for the whole of the 6 week trial. Plasma IGF-1 concentration was significantly reduced on day 1 and remained reduced for the whole of the study.

FIG. 4 thus shows plasma octreotide over time in beagle dogs (3 males+3 females) after s.c. dosing of 15 mg (approx. 1.7 mg/kg) octreotide (3% drug load) in 0.5 ml of the P depot formulation precursor (PC/GDO/EtOH (47.5/47.5/5). Plasma octreotide concentration rapidly reached its maximum, where after the plasma levels slowly decreased to reach a plateau level within a few days. The "burst" (initial release over the first 24 hours) was <10% and plateau was reached within 24 hours. Data is presented as means± standard deviation.

FIG. 5 shows plasma IGF-1 concentration as % of baseline over time in beagle dogs (3 males+3 females) after s.c. dosing of 15 mg (approx. 1.7 mg/kg) octreotide (3% drug load) in 0.5 ml of the P depot formulation precursor (PC/GDO/EtOH (47.5/47.5/5). IGF-1 reached its minimum within 5 days and then remained below baseline values for the remainder of the test period, indicating that octreotide continuously depressed the synthesis/release of this hormone. Data is presented as means± standard deviation.

Unlike PLGA formulations, no lag period was observed between injection and the effects on octreotide & IGF-1 levels being observed. The initial release was less than 10% and plateau plasma level of octreotide was reached within 24 hours.

Example 9

Variation of "Burst" Profile

The initial release profile of three otherwise identical depot precursors was examined by using compositions Q, S and P generated in Example 7. Each of the formulations was injected into a rat model by the protocol described in Example 4. The experiment was constructed for 28 days.

Figure 6:
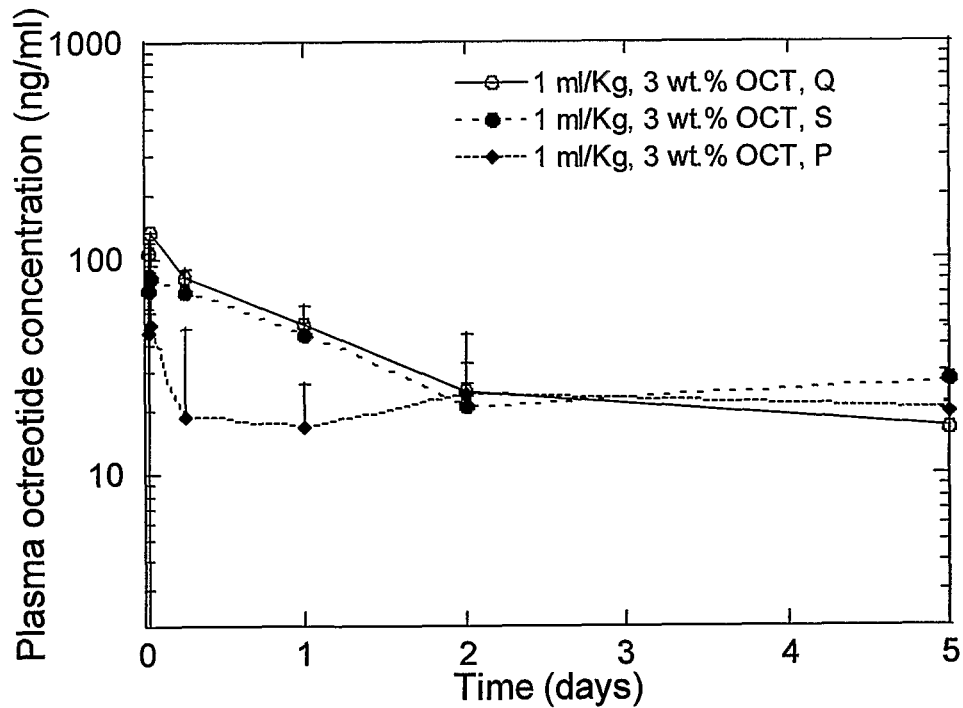
FIG. 6 shows plasma octreotide over time in rats after s.c. dosing of 30 mg/kg octreotide in 1 ml/kg of the P, Q and S.

The release from the three formulations varied significantly in the first 5 days and is shown in FIG. 6. This Figure thus shows plasma octreotide over time in rats after s.c. dosing of 30 mg/kg octreotide (3% drug load) in 1 ml/kg of the P (PC/GDO/EtOH (47.5/47.5/5), Q (PC/GDO/EtOH (45/45/10) and S(PC/GDO/EtOH (46.5/46.5/7) formulation precursors, respectively. N=6 in all groups.

It was found that the composition, particularly the EtOH (component c) could be used to tune the octreotide initial release profile. For the P formulation (5% EtOH), the initial release was less than 10% and plateau was reached within 12 hours. For Q and S, the initial releases were >10% and plateau was not reached until after 48 hours. Data in the Figure are presented as means±standard deviation.

The three compositions showed essentially the same release profiles from day 5 to the end of the study (day 28).

Example 10

Varying Injection Volume

The composition P generated in Example 7 was administered in three injection volumes to study the relationship of dose to plasma concentration.

The protocol for administration in the rat model was as for Example 4 and the results are shown in FIG. 7.

Thus, FIG. 7 shows plasma octreotide over time in rats after s.c. dosing of 9, 30, and 90 mg/kg octreotide (3% drug load) in 0.3, 1, and 3 ml/kg of the P formulation precursor (PC/GDO/EtOH (47.5/47.5/5), respectively. N=8 in all groups.

The initial release was less than 10% and plateau was reached within 48 hours for all doses. There was an unexpected proportionality observed between dose volume (dose) and plasma octreotide concentration (and area under the plasma concentration over time curves). Data in the Figure are presented as means±standard deviation.

LEGENDS TO FIGURES

FIG. 1. Decrease in viscosity of the depot precursor on addition of solvents. PC/GDO (6/4) as a precursor to a reversed hexagonal HII phase and PC/GDO (3/7) is a precursor to a reversed cubic $I_2$ phase.

FIG. 2. Plasma octreotide concentration over 28 days in rats (n=3) after s.c. dosing of 1 ml/kg formulation J (1 wt % OCT). Data is presented as means with standard deviations FIG. 3. Plasma octreotide concentration over 28 days in rats (n=6) after s.c. dosing of 1 ml/kg formulation P (3 wt % OCT).

FIG. 4. Plasma octreotide concentration in the interval 1 hour to 42 days in dogs (n=6) after s.c. dosing of 0.5 ml formulation P (3 wt % OCT).

FIG. 5. Plasma IGF-1 concentration in the interval 1 hour to 42 days in dogs (n=6) after s.c. dosing of 0.5 ml formulation P (3 wt % OCT).

FIG. 6. Plasma octreotide concentration over 5 days in rats after s.c. dosing of 1 ml/kg formulation P (n=6), Q (n=6), and S (n=6), respectively. All formulations contained 3 wt % OCT.

FIG. 7. Plasma octreotide concentration over 28 days in rats after s.c. dosing of formulation P (3 wt % OCT) given as different dosing volumes 0.3, 1, and 3 ml/kg. N=6 for all treatments.

FIG. 8. Plasma octreotide concentration over 6 days in dogs (n=6) after s.c. and i.m dosing of 0.5 mg formulation P (3 wt % OCT).

The invention claimed is:

1. A non liquid-crystalline formulation precursor having a viscosity of between 1-1000 mPas at 20° C. for the in vivo generation of a liquid crystalline lipid composition for the controlled release of at least one somatostatin analogue following parenteral administration, said non liquid-crystalline formulation precursor comprising a mixture of:
   a) 27-67.5 wt. % of at least one diacyl glycerol;
   b) 22.5-63 wt. % of at least one phosphatidyl choline;
   c) at least one oxygen containing organic solvent; and
   d) at least one somatostatin analogue, wherein the at least one somatostatin analogue having somatostatin activity is a cyclic peptide of 14 or fewer amino acids having at least one intra-molecular crosslink and a type-2 β turn;
and wherein the formulation precursor forms at least one liquid crystalline phase structure upon contact with an aqueous fluid.

2. The formulation precursor as claimed in claim 1 which is a formulation precursor comprising a mixture of
   42 to 55.8 parts by weight of glycerol dioleate as component a),
   30 to 46 parts by weight of phosphatidyl choline as component b),
   5 to 10 parts by weight of ethanol as component c), and
   0.5 to 6 parts by weight of octreotide as component d).

3. The formulation precursor as claimed in claim 1 wherein component a) comprises glycerol dioleate.

4. The formulation precursor as claimed in claim 3 wherein component b) comprises at least one of:
   i) soy phosphatidyl choline or
   ii) egg phosphatidyl choline.

5. The formulation precursor as claimed in claim 4 wherein component c) comprises ethanol.

6. The formulation precursor as claimed in claim 5 wherein said formulation precursor comprises at least one somatostatin analogue selected from octreotide, lanreotide and vapreotide.

7. A method for the treatment of a human or non-human mammalian subject in need thereof with a somatostatin analogue, said method comprising administering to said subject a formulation precursor as claimed in claim 1.

8. The method as claimed in claim 7 wherein the method of treatment is a method for the treatment of at least one condition selected from acromegaly, cancers, carcinomas, melanomas, tumours expressing at least one somatostatin receptor, sst(2)-positive tumours, sst(5)-positive tumours, prostate cancers, gastro-entero-pancreatic neuroendocrine (GEP NE) tumours, carcinoid tumours, insulinomas, gastrinomas, vasoactive intestinal peptide (VIP) tumours and glucagonomas, elevated growth hormone (GH), elevated insulin-like growth factor I (IGF-I), varicial bleeding (especially esophageal), chemotherapy induced gastro intestinal problems (such as diarrhea), lymphorrhea, diabetic retinopathy, thyroid eye disease, obesity, pancreatitis, and related conditions.

9. The method as claimed in claim 7 or claim 8 comprising the administration of a formulation precursor comprising a mixture of
   42 to 55.8 parts by weight of glycerol dioleate as component a),
   30 to 46 parts by weight of phosphatidyl choline as component b),
   5 to 10 parts by weight of ethanol as component c), and
   0.5 to 6 parts by weight of octreotide as component d).

10. The method as claimed in claim 7 comprising administration by:
    i) i.m. injection
    ii) s.c. injection;
    iii) deep s.c. injection;
    iv) intravitreal
    v) subconjunctival injection; or
    vi) other parenteral administration routes.

11. The method as claimed in claim 7 comprising administration by means of a pre-filled administration device.

12. The method as claimed in claim 7 comprising administration through a needle no larger than 19 gauge.

13. The method as claimed in claim 7 comprising a single administration every 20 to 90 days.

14. The method of claim 7 where the administered dose is selected by means of the volume injected.

15. A disposable administration device pre-loaded with a measured dose of a non liquid-crystalline formulation precursor for the in vivo generation of a composition for the controlled release of at least one somatostatin analogue, said formulation precursor comprising a low viscosity mixture of:
    a) 27-67.5 wt. % of at least one diacyl glycerol;
    b) 22.5-63 wt. % of at least one phosphatidyl choline;
    c) at least one oxygen containing organic solvent; and
    d) at least one somatostatin analogue, wherein the at least one somatostatin analogue having somatostatin activity is a cyclic peptide of 14 or fewer amino acids having at least one intra-molecular crosslink and a type-2 (3 turn;
wherein the viscosity of the formulation precursor is between 1-1000 mPas at 20° C.

16. The device of claim 15 wherein the device is a syringe or a syringe barrel.

17. The device of claim 15 containing a formulation precursor comprising a mixture of
    42 to 55.8 parts by weight of glycerol dioleate as component a),
    30 to 46 parts by weight of phosphatidyl choline as component b),
    5 to 10 parts by weight of ethanol as component c), and
    0.5 to 6 parts by weight of octreotide as component d).

18. The device of claim 15 comprising a needle no larger than 19 gauge.

19. The device of claim 15 containing a single dose of 1 to 500 mg of the at least one somatostatin analogue of 14 or fewer amino acids having at least one intra-molecular crosslink and a type-2 β turn.

20. The device of claim 15 containing octreotide, in an amount of about 10 to 180 mg.

21. The device of claim 15 containing octreotide in a dosage amount of about 0.2 to 3 mg per day.

22. The device of claim 15 containing a total volume for administration of no more than 5 mL.

23. A kit for the administration of at least one somatostatin analogue, said kit containing a measured dose of a formulation precursor having a viscosity of between 1-1000 mPas at 20° C. and comprising a non liquid-crystalline mixture of:
    a) 27-67.5 wt. % of at least one diacyl glycerol;
    b) 22.5-63 wt. % of at least one phosphatidyl choline;
    c) at least one oxygen containing organic solvent; and
    d) at least one somatostatin analogue, wherein the at least one somatostatin analogue having somatostatin activity is a cyclic peptide of 14 or fewer amino acids having at least one intra-molecular crosslink and a type-2 β turn.

24. The kit of claim 23 including an administration device.

25. The kit of claim 23 containing a formulation precursor comprising a mixture of
    42 to 55.8 parts by weight of glycerol dioleate as component a),
    30 to 46 parts by weight of phosphatidyl choline as component b),
    5 to 10 parts by weight of ethanol as component c), and 0.5 to 6 parts by weight of octreotide as component d); wherein the formulation precursor has a viscosity of between 1-1000 mPas at 20° C.

26. The kit of claim 23 containing a prefilled device.

27. The kit of claim 23 containing a needle no larger than 19 gauge.

28. The kit of claim 23 containing a single dose of 1 to 500 mg of the at least one somatostatin analogue.

29. The kit of claim 23 containing octreotide, in an amount of about 10 to 180 mg.

30. The kit of claim 23 containing octreotide in a dosage amount of about 0.2 to 3 mg per day.

31. The kit of claim 23 containing a total volume for administration of no more than 5 mL.

32. The kit of claim 23 containing instructions for administration by
   i) i.m. injection
   ii) s.c. injection;
   iii) deep s.c. injection;
   iv) intravitreal
   v) subconjunctival injection;
   vi) or other parenteral administration routes.

33. A formulation precursor as claimed in claim 1 comprising a mixture of:
   42 to 55.8 parts by weight of glycerol dioleate as component a);
   30 to 46 parts by weight of phosphatidyl choline as component b);
   5 to 10 parts by weight of ethanol as component c), and
   0.5 to 6 parts by weight of octreotide as component d).

* * * * *